United States Patent [19]
Prockop et al.

[11] Patent Number: 5,948,611
[45] Date of Patent: Sep. 7, 1999

[54] PRIMERS AND METHODS FOR DETECTING MUTATIONS IN THE PROCOLLAGEN II GENE (COL2A1) THAT INDICATE A GENETIC PREDISPOSITION FOR A COL2A1-ASSOCIATED DISEASE

[75] Inventors: Darwin J. Prockop, Philadelphia; Leena Ala-Kokko, Andalusia, both of Pa.; Charlene J. Williams, Sewell, N.J.; Pertti Ritvaniemi, Oulu, Finland; Clinton Baldwin, Cambridge, Mass.; Ian Hopkinson, Wenvoe, United Kingdom; Nilofer Nina Ahmad, Philadelphia, Pa.

[73] Assignee: Thomas Jefferson University, Philadelphia, Pa.

[21] Appl. No.: 08/256,426

[22] PCT Filed: Nov. 12, 1993

[86] PCT No.: PCT/US93/10964

§ 371 Date: Feb. 3, 1995

§ 102(e) Date: Feb. 3, 1995

[87] PCT Pub. No.: WO94/11532

PCT Pub. Date: May 26, 1994

Related U.S. Application Data

[63] Continuation of application No. 07/977,284, Nov. 13, 1992, Pat. No. 5,558,988.

[51] Int. Cl.[6] .............................. C12Q 1/68; C12P 19/34; C07H 21/04
[52] U.S. Cl. ..................... 435/6; 435/91.2; 536/24.31; 536/24.33
[58] Field of Search .................. 435/6, 91.2; 536/24.31, 536/24.33

[56] References Cited

U.S. PATENT DOCUMENTS 5,045,449  9/1991  Ala-Kokko et al. ....................... 435/6

OTHER PUBLICATIONS

Horton et al., Proc. Natl. Acad. Sci. USA 89, 4583–4587 (1992).

Huang et al., Eur. J. Biochem. 195, 593–600 (1991).

Abrams et al., "Comprehensive Detection of Single Base Changes in Human Genomic DNA Using Denaturing Gradient Gel Electrophoresis and a GC Clamp", *Genomics* 7:463–475 (1990).

Ahmad et al., "Stop Codon in the Procollagen II Gene (COL2A1) in a Family with the Stickler Syndrome (Arthro–Ophthalmopathy)", *Proc. Natl. Acad. Sci. USA* 88:6624–6627 (1991).

Ala–Kokko and Prockop, "Completion of the Intron–Exon Structure of the Gene for Human Type II Procollagen (COL2A1): Variations in the Nucleotide Sequences of the Alleles from Three Chromosomes", *Genomics* 8:454–460 (1990).

Ala–Kokko et al. "Single Base Mutation in the Type II Procollagen Gene (COL2A1) as a Cause of Primary Osteoarthritis Associated with a Mild Chondrodysplasia", *Proc. Natl. Acad. Sci. USA* 87:6565–6568 (1990).

Chan and Cole, "Low Basal Transcription of Genes for Tissue–Specific Collagens By Fibroblasts and Lymphoblastoid Cells", *Journal of Biological Chemistry* 266(19):12487–12494 (1991).

(List continued on next page.)

*Primary Examiner*—Kenneth R. Horlick
*Attorney, Agent, or Firm*—Panitch Schwarze Jacobs & Nadel, P.C.

[57] ABSTRACT

The invention provides probes and primers for amplifying certain regions of genes for structural proteins of cartilage and methods for detecting mutations in these genes isolated from the nucleic acid of cells suspected of exhibiting mutant structural protein gene expression or having mutant structural protein genes. The invention also provides methods for determining a genetic predisposition for a disease that alters the structure or function of cartilage because of a mutation in a gene for a structural protein of cartilage in a mammal.

20 Claims, 3 Drawing Sheets

OTHER PUBLICATIONS

Cheah et al., "Identification and Characterization of the Human Type II Collagen Gene (COL2A1)", *Proc. Natl. Acad. Sci. USA* 82:2555–2559 (1985).

Fischer and Lerman, "DNA Fragments Differing by Single Base–Pair Substitutions are Separated in Denaturing Gradient Gels: Correspondence with Melting Theory", *Proc. Natl. Acad. Sci. USA* 80:1579–1583 (1983).

Knowlton et al., "Genetic Linkage Analysis of Hereditary Arthro–Ophthalmopathy (Stickler Syndrome) and the Type II Procollagen Gene", *Am. J. Hum. Genet.* 45:681–688 (1989).

Knowlton et al., "Genetic Linkage of a Polymorphism in the Type II Procollagen Gene (COL2A1) to Primary Osteoarthritis Associated with Mild Chondrodysplasia", *New England Journal of Medicine* 322:526–530 (1990).

Mon–Li Chu, "Collagen: Gene Structure", *Connective Tissue and Its Heritable Disorders*, CRC Press, Boca Raton, FL Chapter 3, Part II, pp. 149–165 (1993).

Maniatis et al., *Molecular Cloning: A Laboratory Manual*, Cold Spring Harbor Laboratory, Cold Spring Harbor, New York, pp. 280–281 (1982).

Myers et al., "Detection and Localization of Single Base Changes by Denaturing Gradient Gel Electrophoresis", *Methods in Enzymology* R. Wu, ed., Academic Press, San Diego, 155:501–527 (1987).

Nunez et al., "Promoter Region of the Human Pro–α1 (II)–Collagen Gene", *Gene* 44:11–16 (1986).

Ritvaniemi et al., "A Fourth Example Suggests that Premature Termination Codons in the COL2A1 Gene Are a Common Cause of the Stickler Syndrome: Analysis of the COL2A1 Gene by Denaturing Gradient Gel Electrophoresis", *Genomics* 17:218–221 (1993).

Sanger et al., "DNA Sequencing With Chain–Terminating Inhibitors", *Proc. Natl. Acad. Sci. USA* 74(12):5463–5467 (1977).

Sangiorgi et al., "Isolation and Partial Characterization of the Entire Human Proα1 (II) Collagen Gene", *Nucl. Acids Res.* 13(7):2207–2225 (1985).

Strom and Upholt, "Isolation and Characterization of Genomic Clones Corresponding to the Human Type II Procollagen Gene", *Nucl. Acids Res.* 12(2):1025–1038 (1984).

Su et al., "Organization of the Exons Coding for Proα1 (II) Collagen N–Propeptide Confirms a Distinct Evolutionary History of this Domain of the Fibrillar Collagen Genes", *Genomics* 4:438–441 (1989).

Upholt, "The Type II Collagen Gene", *Molecular Biology*, CRC Press, Boca Raton, FL, 4:31–49 (1989).

Vikkula and Peltonen, "Structural Analyses of the Polymorphic Area in Type II Collagen Gene", *FEBS Lett.* 250(2):171–174 (1989).

Williams et al., "Detection of Sequence Variants in the Gene for Human Type II Procollagen (COL2A1) by Direct Sequencing of Polymerase Chain Reaction–Amplified Genomic DNA", *Human Mutation* 1:403–416 (1992).

SEQUENCE LISTING (1) GENERAL INFORMATION:

(iii) NUMBER OF SEQUENCES: 293

(2) INFORMATION FOR SEQ ID NO: 1:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: LINEAR (iv) ANTI-SENSE: YES (xi) SEQUENCE DESCRIPTION:  SEQ ID NO: 1:

TGCCTAATAT GTGACTCTTC                                           20

(2) INFORMATION FOR SEQ ID NO: 2:

(i) SEQUENCE CHARACTERISTICS:
       (A) LENGTH: 22
       (B) TYPE: NUCLEIC ACID
       (C) STRANDEDNESS: SINGLE
       (D) TOPOLOGY: LINEAR (iv) ANTI-SENSE: NO (xi) SEQUENCE DESCRIPTION: SEQ ID NO: 2:

AGCCTGTGCT ATCTGCTGCA AT        22

(2) INFORMATION FOR SEQ ID NO: 3:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 3:

AATCCCACTA TGATCTCTGC        20

(2) INFORMATION FOR SEQ ID NO: 4:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 4:

TCCATTGCTT AGGTGT        16

(2) INFORMATION FOR SEQ ID NO: 5:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 5:

CAGTCTTGCT CCTCAAGATA C        21

(2) INFORMATION FOR SEQ ID NO: 6:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 6:

CAGGATGTCT ACAAAGGATG C        21

(2) INFORMATION FOR SEQ ID NO: 7:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 7:

TTGCCCATGG CGTATG        16

(2) INFORMATION FOR SEQ ID NO: 8:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 8:

CATGAGTGAG CCGGTACAGA AG                                  22

(2) INFORMATION FOR SEQ ID NO: 9:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 9:

CAAAGTGGAG GTGTTCAGAG                                    20

(2) INFORMATION FOR SEQ ID NO: 10:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 10:

GTCACTTCTG AGATGAAACG CC                                  22

(2) INFORMATION FOR SEQ ID NO: 11:

(i) SEQUENCE CHARACTERISTICS:
        (A) LENGTH: 15
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 11:

AGCTGTCCAA GTGTG                                          15

(2) INFORMATION FOR SEQ ID NO: 12:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 12:

CAAGTGTGGG GATTCGAGAC AAC                                 23

(2) INFORMATION FOR SEQ ID NO: 13:

(i) SEQUENCE CHARACTERISTICS:

(A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 13:

CCTCCTGCAG CCAGGGCA                                                   18

(2) INFORMATION FOR SEQ ID NO: 14:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 14:

GTATCACGGG TGAGAAG                                                    17

(2) INFORMATION FOR SEQ ID NO: 15:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 15:

TATCACGGGT GAGAAG                                                     16

(2) INFORMATION FOR SEQ ID NO: 16:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 16:

CTTTGGGGTG CGTGCATTTC                                                 20

(2) INFORMATION FOR SEQ ID NO: 17:

(i) SEQUENCE CHARACTERISTICS:
        (A) LENGTH: 15
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 17:

ACTTGGGTTT CCCAG                                                      15

(2) INFORMATION FOR SEQ ID NO: 18:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR

-continued (iv) ANTI-SENSE: YES (xi) SEQUENCE DESCRIPTION: SEQ ID NO: 18:

TCAATCAGAC TTCTGGGAAA CC                    22

(2) INFORMATION FOR SEQ ID NO: 19:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 19:

TCAGCTCGCA CTGACACAAA C                     21

(2) INFORMATION FOR SEQ ID NO: 20:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 20:

TGAAGTTTGT GTCAGTGCGA GC                    22

(2) INFORMATION FOR SEQ ID NO: 21:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 21:

GAGATGACCA GGGCTTTTG                       19

(2) INFORMATION FOR SEQ ID NO: 22:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 22:

ATGACCAGGG CTTTTG                          16

(2) INFORMATION FOR SEQ ID NO: 23:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 23:

CATCAGGAGG TCCTTG                          16

(2) INFORMATION FOR SEQ ID NO: 24:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 24:

CTCCCTCTCC TCTGGTATC                                        19

(2) INFORMATION FOR SEQ ID NO: 25:

(i) SEQUENCE CHARACTERISTICS:
        (A) LENGTH: 15
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 25:

CTCATGCTTA GGCTG                                            15

(2) INFORMATION FOR SEQ ID NO: 26:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 26:

CTAAAGTGCT CGGCAAATGG TG                                    22

(2) INFORMATION FOR SEQ ID NO: 27:

(i) SEQUENCE CHARACTERISTICS:
        (A) LENGTH: 15
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 27:

ATCAGGAGGT CCTTG                                            15

(2) INFORMATION FOR SEQ ID NO: 28:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 28:

TCGCACAGAC ACCAAAACTG CA                                    22

(2) INFORMATION FOR SEQ ID NO: 29:

(i) SEQUENCE CHARACTERISTICS:

(A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 29:

CAGGCACAGT GTGTCCTTCG T                                              21

(2) INFORMATION FOR SEQ ID NO: 30:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 30:

ATACACCCTC GAGACTGCCT TG                                             22

(2) INFORMATION FOR SEQ ID NO: 31:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 31:

CTTTCCAGTA GACATCAGAG TG                                             22

(2) INFORMATION FOR SEQ ID NO: 32:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 32:

CTTCTCACCA CAGATGTAGT CA                                             22

(2) INFORMATION FOR SEQ ID NO: 33:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 33:

GATATGGAGT GAAATCAGTA C                                              21

(2) INFORMATION FOR SEQ ID NO: 34:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 34:

AGTGAAATCA GTACAGA                                                              17

(2) INFORMATION FOR SEQ ID NO: 35:

(i) SEQUENCE CHARACTERISTICS:
            (A) LENGTH: 24
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 35:

GTTGTTGAGG GAGCAATGAG CAAG                                                      24

(2) INFORMATION FOR SEQ ID NO: 36:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 36:

CAGGTGAGAC TGCGAGTGTC TG                                                        22

(2) INFORMATION FOR SEQ ID NO: 37:

(i) SEQUENCE CHARACTERISTICS:
            (A) LENGTH: 24
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 37:

AACTGTGTGT GAACCGACAT GTTC                                                      24

(2) INFORMATION FOR SEQ ID NO: 38:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 38:

CATGTGCATA ATTTAGTGCT GT                                                        22

(2) INFORMATION FOR SEQ ID NO: 39:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 39:

AGTGCTGTCG TTGCAGCTGG                                                           20

(2) INFORMATION FOR SEQ ID NO: 40:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 40:

CACAACTGTC AGAGCAAAGT AC                                      22

(2) INFORMATION FOR SEQ ID NO: 41:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 41:

CAGAATGAAG GTTTGGTGGT TG                                      22

(2) INFORMATION FOR SEQ ID NO: 42:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 42:

CTTGAAACAC ATAGTGGGAA TGTC                                    24

(2) INFORMATION FOR SEQ ID NO: 43:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 43:

CTGAAATGGA CAGCACCTAT G                                      21

(2) INFORMATION FOR SEQ ID NO: 44:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 44:

TGGATCTGGA TCCTGGAG                                              18

(2) INFORMATION FOR SEQ ID NO: 45:

(i) SEQUENCE CHARACTERISTICS:

(A) LENGTH: 15
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 45:

CGTGGACTTT GCTAC                                                             15

(2) INFORMATION FOR SEQ ID NO: 46:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 46:

GAGAGCCCAG TCCTGCCT                                                          18

(2) INFORMATION FOR SEQ ID NO: 47:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 47:

GACTCCAGAG ATGTCAGTGG AAC                                                    23

(2) INFORMATION FOR SEQ ID NO: 48:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 48:

CAGGTCCTCA CACCAGATTC TCTC                                                   24

(2) INFORMATION FOR SEQ ID NO: 49:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 49:

GTTCCACTGA CATCTCTGGA GTCA                                                   24

(2) INFORMATION FOR SEQ ID NO: 50:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 50:

CTCTTTCCCA TGCTCTC                                                              17

(2) INFORMATION FOR SEQ ID NO: 51:

(i) SEQUENCE CHARACTERISTICS:
      (A) LENGTH: 21
      (B) TYPE: NUCLEIC ACID
      (C) STRANDEDNESS: SINGLE
      (D) TOPOLOGY: LINEAR (iv) ANTI-SENSE: YES (xi) SEQUENCE DESCRIPTION: SEQ ID NO: 51:

CTGTGCCTCA TAGAACAGCA G                                                         21

(2) INFORMATION FOR SEQ ID NO: 52:

(i) SEQUENCE CHARACTERISTICS:
      (A) LENGTH: 24
      (B) TYPE: NUCLEIC ACID
      (C) STRANDEDNESS: SINGLE
      (D) TOPOLOGY: LINEAR (iv) ANTI-SENSE: YES (xi) SEQUENCE DESCRIPTION: SEQ ID NO: 52:

CATAATCTGA AAGGACCCAG ATTG                                                      24

(2) INFORMATION FOR SEQ ID NO: 53:

(i) SEQUENCE CHARACTERISTICS:
      (A) LENGTH: 24
      (B) TYPE: NUCLEIC ACID
      (C) STRANDEDNESS: SINGLE
      (D) TOPOLOGY: LINEAR (iv) ANTI-SENSE: YES (xi) SEQUENCE DESCRIPTION: SEQ ID NO: 53:

GTTAAGTCTC CTCCAGGCAT AATC                                                      24

(2) INFORMATION FOR SEQ ID NO: 54:

(i) SEQUENCE CHARACTERISTICS:
      (A) LENGTH: 23
      (B) TYPE: NUCLEIC ACID
      (C) STRANDEDNESS: SINGLE
      (D) TOPOLOGY: LINEAR (iv) ANTI-SENSE: YES (xi) SEQUENCE DESCRIPTION: SEQ ID NO: 54:

GAAGCTGTAT CTGGGCCTTC TCA                                                       23

(2) INFORMATION FOR SEQ ID NO: 55:

(i) SEQUENCE CHARACTERISTICS:
      (A) LENGTH: 20
      (B) TYPE: NUCLEIC ACID
      (C) STRANDEDNESS: SINGLE
      (D) TOPOLOGY: LINEAR (iv) ANTI-SENSE: NO (xi) SEQUENCE DESCRIPTION: SEQ ID NO: 55:

GTGAACAGTT GGATCTTTAG                                                           20

(2) INFORMATION FOR SEQ ID NO: 56:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 56:

CTTTATGGCC TCTCGTCCTC AAG                                               23

(2) INFORMATION FOR SEQ ID NO: 57:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 57:

CTGAAACAGT TGCCAAGGCT AC                                                22

(2) INFORMATION FOR SEQ ID NO: 58:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 58:

CAGTTGCCAA GGCTACTTC                                                    19

(2) INFORMATION FOR SEQ ID NO: 59:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 59:

CTTCATACTC TAGATC                                                          16

(2) INFORMATION FOR SEQ ID NO: 60:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 60:

TCCAAGGCCA GGTGAAGG                                                   18

(2) INFORMATION FOR SEQ ID NO: 61:

(i) SEQUENCE CHARACTERISTICS:

(A) LENGTH: 22
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 61:

CAGAACACGG ACCACAAGGA CT                                        22

(2) INFORMATION FOR SEQ ID NO: 62:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 62:

GAGAAAGAGG AGGATGACAT G                                         21

(2) INFORMATION FOR SEQ ID NO: 63:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 63:

GTCTGAGCTC CTTCCCAGGA A                                         21

(2) INFORMATION FOR SEQ ID NO: 64:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 64:

CAGAAGTTAA CCTCTGAGAA TC                                        22

(2) INFORMATION FOR SEQ ID NO: 65:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 65:

GTTAACCTCT GAGAATCCTG                                           20

(2) INFORMATION FOR SEQ ID NO: 66:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE:  NO (xi) SEQUENCE DESCRIPTION:  SEQ ID NO: 66:

GTTGGTGGGT TAGTGGGATG                                                    20

(2) INFORMATION FOR SEQ ID NO: 67:

(i) SEQUENCE CHARACTERISTICS:
          (A) LENGTH: 18
          (B) TYPE: NUCLEIC ACID
          (C) STRANDEDNESS:  SINGLE
          (D) TOPOLOGY: LINEAR (iv) ANTI-SENSE:  NO (xi) SEQUENCE DESCRIPTION:  SEQ ID NO: 67:

CAGGTCAAGA TGGTCTGG                                                      18

(2) INFORMATION FOR SEQ ID NO: 68:

(i) SEQUENCE CHARACTERISTICS:
          (A) LENGTH: 20
          (B) TYPE: NUCLEIC ACID
          (C) STRANDEDNESS:  SINGLE
          (D) TOPOLOGY: LINEAR (iv) ANTI-SENSE:  NO (xi) SEQUENCE DESCRIPTION:  SEQ ID NO: 68:

GAGTGGGAGA AGAGGGGCTG                                                    20

(2) INFORMATION FOR SEQ ID NO: 69:

(i) SEQUENCE CHARACTERISTICS:
          (A) LENGTH: 19
          (B) TYPE: NUCLEIC ACID
          (C) STRANDEDNESS:  SINGLE
          (D) TOPOLOGY: LINEAR (iv) ANTI-SENSE:  NO (xi) SEQUENCE DESCRIPTION:  SEQ ID NO: 69:

CTTGG CTTCA GACCC TCAG                                                   19

(2) INFORMATION FOR SEQ ID NO: 70:

(i) SEQUENCE CHARACTERISTICS:
          (A) LENGTH: 20
          (B) TYPE: NUCLEIC ACID
          (C) STRANDEDNESS:  SINGLE
          (D) TOPOLOGY: LINEAR (iv) ANTI-SENSE:  NO (xi) SEQUENCE DESCRIPTION:  SEQ ID NO: 70:

CTCCTTCCAG CCCTGCACTG                                                    20

(2) INFORMATION FOR SEQ ID NO: 71:

(i) SEQUENCE CHARACTERISTICS:
          (A) LENGTH: 18
          (B) TYPE: NUCLEIC ACID
          (C) STRANDEDNESS:  SINGLE
          (D) TOPOLOGY: LINEAR (iv) ANTI-SENSE:  NO (xi) SEQUENCE DESCRIPTION:  SEQ ID NO: 71:

CTCAGAGGAT AGACTTAC                                                      18

(2) INFORMATION FOR SEQ ID NO: 72:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 72:

CATCT CTCTT TTCCC TTGCT TC                                     22

(2) INFORMATION FOR SEQ ID NO: 73:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 73:

GCCTCCCTAA CCCAAACTCC ATCT                                  24

(2) INFORMATION FOR SEQ ID NO: 74:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 74:

TAGATGCTGA GCATGTGTGG                                         20

(2) INFORMATION FOR SEQ ID NO: 75:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 75:

CTTAGTGGAT GTTGGGTGGA T                                        21

(2) INFORMATION FOR SEQ ID NO: 76:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 76:

TTGGCTGTCC ATCAGGATGT                                         20

(2) INFORMATION FOR SEQ ID NO: 77:

(i) SEQUENCE CHARACTERISTICS:

```
            (A) LENGTH: 21
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 77:

GATCAACACT CAATACTGAG G                                              21

(2) INFORMATION FOR SEQ ID NO: 78:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 78:

GTTGATCTCT GTGGCTAGAC                                                20

(2) INFORMATION FOR SEQ ID NO: 79:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 79:

GCTTCCATGC TGAGAACAGC                                                20

(2) INFORMATION FOR SEQ ID NO: 80:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 80:

GTGTGGAAAT GGAGCTCAGC                                                20

(2) INFORMATION FOR SEQ ID NO: 81:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 81:

TCTGGTGTAT CAGCTCAGCC                                                20

(2) INFORMATION FOR SEQ ID NO: 82:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR
```

(iv) ANTI-SENSE: NO (xi) SEQUENCE DESCRIPTION: SEQ ID NO: 82:

TGAGTGGTGC AGGAAGACGC                                                          20

(2) INFORMATION FOR SEQ ID NO: 83:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 83:

ACCGATAGTG CCAAGAAAGC TGC                                                      23

(2) INFORMATION FOR SEQ ID NO: 84:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 84:

GCTCGATGCC TGGACACTGC                                                          20

(2) INFORMATION FOR SEQ ID NO: 85:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 85:

CGAAGTGACC AAGCGTTAGC A                                                        21

(2) INFORMATION FOR SEQ ID NO: 86:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 86:

CCTCAGTATT GAGTGTTGAT C                                                        21

(2) INFORMATION FOR SEQ ID NO: 87:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 87:

```
CTGGACAGCA GCAGGCACTA TC                                                22

(2) INFORMATION FOR SEQ ID NO: 88:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 88:

CACACCTCTT GCAGTGTCCA G                                                 21

(2) INFORMATION FOR SEQ ID NO: 89:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 89:

CTGTCACTGC TGCTGCTTCC                                                   20

(2) INFORMATION FOR SEQ ID NO: 90:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 90:

GGTCTGCCCT ATACTGT                                                      17

(2) INFORMATION FOR SEQ ID NO: 91:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 91:

GGTCTGCCCT ATACTGTG                                                     18

(2) INFORMATION FOR SEQ ID NO: 92:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 92:

GGCAGCAAAC TCACTC                                                       16

(2) INFORMATION FOR SEQ ID NO: 93:

(i) SEQUENCE CHARACTERISTICS:
```

(A) LENGTH: 19
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 93:

GACTCCAGGC TACCACGAA                                            19

(2) INFORMATION FOR SEQ ID NO: 94:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 94:

CATGGAGGAG TGATATTC                                             18

(2) INFORMATION FOR SEQ ID NO: 95:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 95:

CTGCTGTGGA GAATTGTTC                                            19

(2) INFORMATION FOR SEQ ID NO: 96:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 96:

TGCTGTGGAG AATTGTTC                                             18

(2) INFORMATION FOR SEQ ID NO: 97:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 97:

CAATGCGGGC TGCCTCCTTG                                           20

(2) INFORMATION FOR SEQ ID NO: 98:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 98:

AATGCGGGCT GCCTCCTT                                                         18

(2) INFORMATION FOR SEQ ID NO: 99:

(i) SEQUENCE CHARACTERISTICS:
                  (A) LENGTH: 18
                  (B) TYPE: NUCLEIC ACID
                  (C) STRANDEDNESS: SINGLE
                  (D) TOPOLOGY: LINEAR (iv) ANTI-SENSE: NO (xi) SEQUENCE DESCRIPTION: SEQ ID NO: 99:

TGCTCCTTTC CCCACCTC                                                         18

(2) INFORMATION FOR SEQ ID NO: 100:

(i) SEQUENCE CHARACTERISTICS:
                  (A) LENGTH: 17
                  (B) TYPE: NUCLEIC ACID
                  (C) STRANDEDNESS: SINGLE
                  (D) TOPOLOGY: LINEAR (iv) ANTI-SENSE: NO (xi) SEQUENCE DESCRIPTION: SEQ ID NO: 100:

TGCTCCTTTC CCCACCT                                                          17

(2) INFORMATION FOR SEQ ID NO: 101:

(i) SEQUENCE CHARACTERISTICS:
                  (A) LENGTH: 18
                  (B) TYPE: NUCLEIC ACID
                  (C) STRANDEDNESS: SINGLE
                  (D) TOPOLOGY: LINEAR (iv) ANTI-SENSE: NO (xi) SEQUENCE DESCRIPTION: SEQ ID NO: 101:

CTGCTTCTCC CTGGACCT                                                         18

(2) INFORMATION FOR SEQ ID NO: 102:

(i) SEQUENCE CHARACTERISTICS:
                  (A) LENGTH: 20
                  (B) TYPE: NUCLEIC ACID
                  (C) STRANDEDNESS: SINGLE
                  (D) TOPOLOGY: LINEAR (iv) ANTI-SENSE: YES (xi) SEQUENCE DESCRIPTION: SEQ ID NO: 102:

GACTCCAGGC TACCACGAAG                                                       20

(2) INFORMATION FOR SEQ ID NO: 103:

(i) SEQUENCE CHARACTERISTICS:
                  (A) LENGTH: 20
                  (B) TYPE: NUCLEIC ACID
                  (C) STRANDEDNESS: SINGLE
                  (D) TOPOLOGY: LINEAR (iv) ANTI-SENSE: YES (xi) SEQUENCE DESCRIPTION: SEQ ID NO: 103:

CCAGGCATTC CCTGAAGACC                                                       20

(2) INFORMATION FOR SEQ ID NO: 104:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 104:

AGCCACAGCT TTGGTGA                                    17

(2) INFORMATION FOR SEQ ID NO: 105:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 105:

CGGGCTCAGG AGGAATGAAG                              20

(2) INFORMATION FOR SEQ ID NO: 106:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 106:

AGGAATGAAG AAGAACAGAA GTG                        23

(2) INFORMATION FOR SEQ ID NO: 107:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 107:

CTGGTTACCC AGGCTCCATG                              20

(2) INFORMATION FOR SEQ ID NO: 108:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 108:

TGATGAAGGT TTCTGTTAGC                              20

(2) INFORMATION FOR SEQ ID NO: 109:

(i) SEQUENCE CHARACTERISTICS:

(A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 109:

TCATCACCAG GTGCCATAAG                    20

(2) INFORMATION FOR SEQ ID NO: 110:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 110:

GATCCTAATG CCCAGCAGT                     19

(2) INFORMATION FOR SEQ ID NO: 111:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 111:

GCTGGGCATT AGGATCCAGC                    20

(2) INFORMATION FOR SEQ ID NO: 112:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 112:

GTCTGGGCAG TCTGCCACTG                    20

(2) INFORMATION FOR SEQ ID NO: 113:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 113:

GCAACTGCAG GGACTTCTCT                    20

(2) INFORMATION FOR SEQ ID NO: 114:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 114:
                    GCTGCACAGT AACACAGGCT    20

(2) INFORMATION FOR SEQ ID NO: 115:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 115:

ACTGACTCCC TGGCTCTCTG                                                    20

(2) INFORMATION FOR SEQ ID NO: 116:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 116:

GCAGGCAGAG GCTCTGTTAA                                                    20

(2) INFORMATION FOR SEQ ID NO: 117:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 117:

GCACGTCACT CCCATCATGT                                                    20

(2) INFORMATION FOR SEQ ID NO: 118:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 118:

TTAACAGAGC CTCTGCCTGC                                                    20

(2) INFORMATION FOR SEQ ID NO: 119:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 119:

AGCAGAAGCA GGTCCAGGCA G                                                  21

(2) INFORMATION FOR SEQ ID NO: 120:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 120:

CGCAGATACT CACAGAGTCT                                                   20

(2) INFORMATION FOR SEQ ID NO: 121:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 121:

CTGCGAACCA TCCTCTGCGC                                                   20

(2) INFORMATION FOR SEQ ID NO: 122:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 122:

CAGGAGATCA GCAGCTTGGT                                                   20

(2) INFORMATION FOR SEQ ID NO: 123:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 123:

ACCAAGCTGC TGATCTCCTG                                                   20

(2) INFORMATION FOR SEQ ID NO: 124:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 124:

TTTAGTGCCA AGAAAGCTGC                                                   20

(2) INFORMATION FOR SEQ ID NO: 125:

(i) SEQUENCE CHARACTERISTICS:
        (A) LENGTH: 20
        (B) TYPE: NUCLEIC ACID (C) STRANDEDNESS: SINGLE
            (D) TOPOLOGY: LINEAR (iv) ANTI-SENSE: NO (xi) SEQUENCE DESCRIPTION: SEQ ID NO: 125:

ACAGAAGCCC ACCGTCTTCC                                               20

(2) INFORMATION FOR SEQ ID NO: 126:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 126:

ACAGCCTGTG CCTGCTTCTA TG                                            22

(2) INFORMATION FOR SEQ ID NO: 127:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 127:

CTGTGCCTGC TTCTATGACC AGA                                           23

(2) INFORMATION FOR SEQ ID NO: 128:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 128:

CTTTCCATAC CAGGCTCTGA GA                                            22

(2) INFORMATION FOR SEQ ID NO: 129:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 129:

TCCATACCAG GCTCTGAGAC                                               20

(2) INFORMATION FOR SEQ ID NO: 130:

(i) SEQUENCE CHARACTERISTICS:
            (A) LENGTH: 17
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 130:

CATACCAGGC TCTGAGA                                                              17

(2) INFORMATION FOR SEQ ID NO: 131:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 131:

GAACGGACTC AGAGGAGTGA AG                                                        22

(2) INFORMATION FOR SEQ ID NO: 132:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 132:

TCAGTTAGCT ACTCCTCCAG                                                           20

(2) INFORMATION FOR SEQ ID NO: 133:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 133:

CCAGTGAGTT CATCACCACT                                                           20

(2) INFORMATION FOR SEQ ID NO: 134:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 134:

TGTCTCACAT GGTGAGAAGG TTG                                                       23

(2) INFORMATION FOR SEQ ID NO: 135:

(i) SEQUENCE CHARACTERISTICS:
            (A) LENGTH: 22
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 135:

CAGAGAGGAA ACTGCTGTCA CT                                                        22

(2) INFORMATION FOR SEQ ID NO: 136:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 136:

TGAGGCCACA GTGACTTTG                                               19

(2) INFORMATION FOR SEQ ID NO: 137:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 137:

CTTCTGAGCT CACAGA                                                  16

(2) INFORMATION FOR SEQ ID NO: 138:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 138:

GACAGAGCTG TGCTGAGA                                               18

(2) INFORMATION FOR SEQ ID NO: 139:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 139:

TGAGGGAGGT AGAAGCCTTG                                          20

(2) INFORMATION FOR SEQ ID NO: 140:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 140:

CTTCAGGAGA GGGCAGACAA G                                        21

(2) INFORMATION FOR SEQ ID NO: 141:

(i) SEQUENCE CHARACTERISTICS:
        (A) LENGTH: 20
        (B) TYPE: NUCLEIC ACID (C) STRANDEDNESS: SINGLE
            (D) TOPOLOGY: LINEAR (iv) ANTI-SENSE: NO (xi) SEQUENCE DESCRIPTION: SEQ ID NO: 141:

CAAGGCTTCT ACCTCCCTCA                                                      20

(2) INFORMATION FOR SEQ ID NO: 142:

(i) SEQUENCE CHARACTERISTICS:
            (A) LENGTH: 19
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 142:

TCAGGAACTG TCCCCTTGT                                                       19

(2) INFORMATION FOR SEQ ID NO: 143:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 143:

CTTGTCTGCC CTCTCCTGAA G                                                    21

(2) INFORMATION FOR SEQ ID NO: 144:

(i) SEQUENCE CHARACTERISTICS:
            (A) LENGTH: 18
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 144:

CAAAGTGTGA GTGAGTTG                                                        18

(2) INFORMATION FOR SEQ ID NO: 145:

(i) SEQUENCE CHARACTERISTICS:
            (A) LENGTH: 24
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 145:

TCTAGGCTGA GAGAGACTTT GTTC                                                 24

(2) INFORMATION FOR SEQ ID NO: 146:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 146:

CTTCTAGGCT GAGATGAGAC TTG                                           23

(2) INFORMATION FOR SEQ ID NO: 147:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 147:

GTTGGAACAA GTCTCATCTC A                                             21

(2) INFORMATION FOR SEQ ID NO: 148:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 148:

GAACAAGTCT CATCTCA                                                  17

(2) INFORMATION FOR SEQ ID NO: 149:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 149:

CATCTCAGCC TAGAAG                                                   16

(2) INFORMATION FOR SEQ ID NO: 150:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 150:

CAGTCTCTGG ACTAAG                                                   16

(2) INFORMATION FOR SEQ ID NO: 151:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 151:

GAGCAGTGGC CTCAGATG                                                 18

(2) INFORMATION FOR SEQ ID NO: 152:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 152:

GTCCCACCCA AGCTGAGGAA TC                                        22

(2) INFORMATION FOR SEQ ID NO: 153:

(i) SEQUENCE CHARACTERISTICS:
        (A) LENGTH: 25
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 153:

GACAGACACC GATTGAGTCA GGTCA                                     25

(2) INFORMATION FOR SEQ ID NO: 154:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 154:

GAACAAGACA GACACCGATT G                                         21

(2) INFORMATION FOR SEQ ID NO: 155:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 155:

TCCGCAGTCT CTGGACTAAG                                           20

(2) INFORMATION FOR SEQ ID NO: 156:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 156:

TGAGTATCCA AGTGTCCTGC                                           20

(2) INFORMATION FOR SEQ ID NO: 157:

(i) SEQUENCE CHARACTERISTICS:
        (A) LENGTH: 20
        (B) TYPE: NUCLEIC ACID (C) STRANDEDNESS: SINGLE
            (D) TOPOLOGY: LINEAR (iv) ANTI-SENSE: NO (xi) SEQUENCE DESCRIPTION: SEQ ID NO: 157:

ATATGTCTGT GCTGACCGTG                                           20

(2) INFORMATION FOR SEQ ID NO: 158:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO: 158:

TCTGTCTGAC AGCGGAGGCA                                           20

(2) INFORMATION FOR SEQ ID NO: 159:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 159:

GGGATTCCTC AGCCTGGGTG                                           20

(2) INFORMATION FOR SEQ ID NO: 160:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 160:

ACTGAGCATG TGAAGAACTG                                           20

(2) INFORMATION FOR SEQ ID NO: 161:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 161:

TATCAGGACA GCCACCTACC                                           20

(2) INFORMATION FOR SEQ ID NO: 162:

(i) SEQUENCE CHARACTERISTICS:
            (A) LENGTH: 20
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 162:

ACACTCTAGT ACATTCTAGC                              20

(2) INFORMATION FOR SEQ ID NO: 163:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 163:

AACCCTCTGG CGGAAACTTC                              20

(2) INFORMATION FOR SEQ ID NO: 164:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 164:

CTAAGGAAGA AATAGACATG                              20

(2) INFORMATION FOR SEQ ID NO: 165:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 165:

GAAGAAATAG ACATGGTGCT GT                           22

(2) INFORMATION FOR SEQ ID NO: 166:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 166:

GACACTCTAG TACATTC                                 17

(2) INFORMATION FOR SEQ ID NO: 167:

(i) SEQUENCE CHARACTERISTICS:
        (A) LENGTH: 16
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 167:

CTCTAGTACA TTCTAG                                  16

(2) INFORMATION FOR SEQ ID NO: 168:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 168:

GTACATTCTA GCAAATG                                                17

(2) INFORMATION FOR SEQ ID NO: 169:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 169:

CATCTCCTCC CTTGCTGCTA G                                           21

(2) INFORMATION FOR SEQ ID NO: 170:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 170:

ATGGAGTCCA CCCTGAGGTC                                             20

(2) INFORMATION FOR SEQ ID NO: 171:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 171:

CTTAGGGCTG GACTTAGCTC                                             20

(2) INFORMATION FOR SEQ ID NO: 172:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 172:

ATCCCTTGTC CCTGTAGGCC                                             20

(2) INFORMATION FOR SEQ ID NO: 173:

(i) SEQUENCE CHARACTERISTICS:
        (A) LENGTH: 20
        (B) TYPE: NUCLEIC ACID (C) STRANDEDNESS: SINGLE
          (D) TOPOLOGY: LINEAR (iv) ANTI-SENSE: NO (xi) SEQUENCE DESCRIPTION: SEQ ID NO: 173:

CAGGCCTGGG TCTCTCAAGC                                              20

(2) INFORMATION FOR SEQ ID NO: 174:

(i) SEQUENCE CHARACTERISTICS:
          (A) LENGTH: 20
          (B) TYPE: NUCLEIC ACID
          (C) STRANDEDNESS: SINGLE
          (D) TOPOLOGY: LINEAR (iv) ANTI-SENSE: NO (xi) SEQUENCE DESCRIPTION: SEQ ID NO: 174:

CCTTGAACCA TGAACTCTTG                                              20

(2) INFORMATION FOR SEQ ID NO: 175:

(i) SEQUENCE CHARACTERISTICS:
          (A) LENGTH: 20
          (B) TYPE: NUCLEIC ACID
          (C) STRANDEDNESS: SINGLE
          (D) TOPOLOGY: LINEAR (iv) ANTI-SENSE: YES (xi) SEQUENCE DESCRIPTION: SEQ ID NO: 175:

TCTCTCACCT GTCACTCAGC                                              20

(2) INFORMATION FOR SEQ ID NO: 176:

(i) SEQUENCE CHARACTERISTICS:
          (A) LENGTH: 20
          (B) TYPE: NUCLEIC ACID
          (C) STRANDEDNESS: SINGLE
          (D) TOPOLOGY: LINEAR (iv) ANTI-SENSE: YES (xi) SEQUENCE DESCRIPTION: SEQ ID NO: 176:

TCTCTCACCT GTCACTCAGC                                              20

(2) INFORMATION FOR SEQ ID NO: 177:

(i) SEQUENCE CHARACTERISTICS:
          (A) LENGTH: 20
          (B) TYPE: NUCLEIC ACID
          (C) STRANDEDNESS: SINGLE
          (D) TOPOLOGY: LINEAR (iv) ANTI-SENSE: NO (xi) SEQUENCE DESCRIPTION: SEQ ID NO: 177:

TGGAGAGGCC TTTGGCAAGC                                              20

(2) INFORMATION FOR SEQ ID NO: 178:

(i) SEQUENCE CHARACTERISTICS:
          (A) LENGTH: 20
          (B) TYPE: NUCLEIC ACID
          (C) STRANDEDNESS: SINGLE
          (D) TOPOLOGY: LINEAR (iv) ANTI-SENSE: NO (xi) SEQUENCE DESCRIPTION: SEQ ID NO: 178:

TTGTGGGCTC TGATGCTCGC                                                      20

(2) INFORMATION FOR SEQ ID NO: 179:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: YES (xi) SEQUENCE DESCRIPTION: SEQ ID NO: 179:

TCAGGTCAGC CATTCAGTGC                                                      20

(2) INFORMATION FOR SEQ ID NO: 180:

(i) SEQUENCE CHARACTERISTICS:
        (A) LENGTH: 70
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 180:

CCGCCCGCCC CGCCCGCCGC CCGCCCCGCC CGCCGCCCGC TCTTGGAGAA                     50

ACACTGCTTC CCATTGATGC                                                      70

(2) INFORMATION FOR SEQ ID NO: 181:

(i) SEQUENCE CHARACTERISTICS:
        (A) LENGTH: 30
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 181:

AAAAGCCACA TTTCTGGAGG GACAGCCTGA                                           30

(2) INFORMATION FOR SEQ ID NO: 182:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 182:

CCGCCCGCCC CGCCCGCCGC CCGCCCCGCC CGCCGCCCGC CTAGTGCCTT                     50

TCAACCTCCT AACGTTG                                                         67

(2) INFORMATION FOR SEQ ID NO: 183:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 183:

```
AGGTTGTCAG ACTCTCTGGC TCTACTAAG                                     29

(2) INFORMATION FOR SEQ ID NO: 184:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 184:

CCGCCCGCCC CGCCCGCCGC CCGCCCCGCC CGCCGCCCGC GTAAACCCCT              50

CATTTTCTGT TCCGATGC                                                 68

(2) INFORMATION FOR SEQ ID NO: 185:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 185:

CAGCTGCGTC CTAGTGGTCT ATCATTAG                                      28

(2) INFORMATION FOR SEQ ID NO: 186:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 186:

GTCCATTGCT TAGGTGTCTT CCCACTA                                       27

(2) INFORMATION FOR SEQ ID NO: 187:

(i) SEQUENCE CHARACTERISTICS:
        (A) LENGTH: 66
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 187:

CCGCCCGCCC CGCCCGCCGC CCGCCCCGCC CGCCGCCCGC GGAGGCAGCT              50

CCTCATTTGT CTACTC                                                   66

(2) INFORMATION FOR SEQ ID NO: 188:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 188:
```

CCGCCCGCCC CGCCCGCCGC CCGCCCCGCC CGCCGCCCGC CACTATGCTA         50

CGCGTCTCTG AGGAAGCT                                            68

(2) INFORMATION FOR SEQ ID NO: 189:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 189:

CTCAGAAGTG ACCTCATTGA ACTGGATGC                                29

(2) INFORMATION FOR SEQ ID NO: 190:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 190:

CCGCCCGCCC CGCCCGCCGC CCGCCCCGCC CGCCGCCCGC CTCCTGCAGC         50

CAGGGCAGCT TTCCACT                                             67

(2) INFORMATION FOR SEQ ID NO: 191:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 191:

GGAAGAAATG CACGCACCCC AAAGTGC                                  27

(2) INFORMATION FOR SEQ ID NO: 192:

(i) SEQUENCE CHARACTERISTICS:
        (A) LENGTH: 66
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 192:

CCGCCCGCCC CGCCCGCCGC CCGCCCCGCC CGCCGCCCGC CCAACTTGGG         50

TTTCCCAGAA GTCTGA                                              66

(2) INFORMATION FOR SEQ ID NO: 193:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 193:

TTGTCTCCCT CCTCCCCATC CCATTGTAC                                    29

(2) INFORMATION FOR SEQ ID NO: 194:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 194:

CCGCCCGCCC CGCCCGCCGC CCGCCCCGCC CGCCGCCCGC ACCACTGAAG             50

TTTGTGTCAG TGCGAGCT                                                68

(2) INFORMATION FOR SEQ ID NO: 195:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 195:

TTTGCAGCCA TCTGATAGTC TGAAGAGTC                                    29

(2) INFORMATION FOR SEQ ID NO: 196:

(i) SEQUENCE CHARACTERISTICS:
        (A) LENGTH: 69
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 196:

CCGCCCGCCC CGCCCGCCGC CCGCCCCGCC CGCCGCCCGC CACCCTGAGC             50

ACCGTAAAGC CAACTCATG                                               69

(2) INFORMATION FOR SEQ ID NO: 197:

(i) SEQUENCE CHARACTERISTICS:
        (A) LENGTH: 30
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 197:

CTATGCCTCA CAGGTTTGTT TCGAGGGTCA                                   30

(2) INFORMATION FOR SEQ ID NO: 198:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 198:

```
TGCCTTCTGG CCACCCACTC GCACAGA                                            27

(2) INFORMATION FOR SEQ ID NO: 199:

(i) SEQUENCE CHARACTERISTICS:
         (A) LENGTH: 70
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 199:

CCGCCCGCCC CGCCCGCCGC CCGCCCCGCC CGCCGCCCGC CCACCCACTC                   50

GCACAGACAC CAAAACTGCA                                                    70

(2) INFORMATION FOR SEQ ID NO: 200:

(i) SEQUENCE CHARACTERISTICS:
         (A) LENGTH: 30
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 200:

GTGGTTGCAC CCAATACACC CTCGAGACTG                                         30

(2) INFORMATION FOR SEQ ID NO: 201:

(i) SEQUENCE CHARACTERISTICS:
         (A) LENGTH: 70
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 201:

CCGCCCGCCC CGCCCGCCGC CCGCCCCGCC CGCCGCCCGC TTGCTTTGCC                   50

TTCTGAAGCC AGGCAAAGCT                                                    70

(2) INFORMATION FOR SEQ ID NO: 202:

(i) SEQUENCE CHARACTERISTICS:
         (A) LENGTH: 29
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 202:

AGCTTCTCGG CACCCAGAAG TTCCTGACT                                          29

(2) INFORMATION FOR SEQ ID NO: 203:

(i) SEQUENCE CHARACTERISTICS:
         (A) LENGTH: 68
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 203:

CCGCCCGCCC CGCCCGCCGC CCGCCCCGCC CGCCGCCCGC TATTGCCCAC                   50
```

```
CCACTAGAGG TCTGTGTC                                                68
```

(2) INFORMATION FOR SEQ ID NO: 204:

(i) SEQUENCE CHARACTERISTICS:
        (A) LENGTH: 30
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 204:

```
CCCACAACTG TCAGAGCAAA GTACAGAGTC                                   30
```

(2) INFORMATION FOR SEQ ID NO: 205:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 205:

```
CCGCCCGCCC CGCCCGCCGC CCGCCCCGCC CGCCGCCCGC GGTGGTTGGG             50

GTTCATTCTT TGCTGCT                                                 67
```

(2) INFORMATION FOR SEQ ID NO: 206:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 206:

```
GGGCTCTCCT GGGGTAGCAA AGTCCAC                                      27
```

(2) INFORMATION FOR SEQ ID NO: 207:

(i) SEQUENCE CHARACTERISTICS:
        (A) LENGTH: 69
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 207:

```
CCGCCCGCCC CGCCCGCCGC CCGCCCCGCC CGCCGCCCGC GGATCTGCTG             50

TGAGTGTTGC CCGTGGACT                                               69
```

(2) INFORMATION FOR SEQ ID NO: 208:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 208:

```
AGAGCATGGG AAAGAGGGGT GATG                                           24

(2) INFORMATION FOR SEQ ID NO: 209:

(i) SEQUENCE CHARACTERISTICS:
        (A) LENGTH: 69
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 209:

CCGCCCGCCC CGCCCGCCGC CCGCCCCGCC CGCCGCCCGC TCCCTGGAGA              50

GAATCTGGTG TGAGGACCT                                                69

(2) INFORMATION FOR SEQ ID NO: 210:

(i) SEQUENCE CHARACTERISTICS:
        (A) LENGTH: 30
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 210:

CTCAGTCCCT GTTAAGTCTC CTCCAGGCAT                                    30

(2) INFORMATION FOR SEQ ID NO: 211:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 211:

GGCTACTTCC TTCATACTCT AGATCGA                                       27

(2) INFORMATION FOR SEQ ID NO: 212:

(i) SEQUENCE CHARACTERISTICS:
        (A) LENGTH: 70
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 212:

CCGCCCGCCC CGCCCGCCGC CCGCCCCGCC CGCCGCCCGC CGGACCACAA              50

GGACTCCACT TCCCTCTCGA                                               70

(2) INFORMATION FOR SEQ ID NO: 213:

(i) SEQUENCE CHARACTERISTICS:
        (A) LENGTH: 70
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 213:

CCGCCCGCCC CGCCCGCCGC CCGCCCCGCC CGCCGCCCGC CTGGCTGGGT              50
```

```
TGGGCTGTTC TCACTCACTG                                                  70

(2) INFORMATION FOR SEQ ID NO: 214:

(i) SEQUENCE CHARACTERISTICS:
         (A) LENGTH: 30
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 214:

CTGAAGCCAA GGGCAACAGC AGCTCTGCTA                                       30

(2) INFORMATION FOR SEQ ID NO: 215:

(i) SEQUENCE CHARACTERISTICS:
         (A) LENGTH: 70
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 215:

CCGCCCGCCC CGCCCGCCGC CCGCCCCGCC CGCCGCCCGC TAGCAGAGCT                 50

GCTGTTGCCC TTGGCTTCAG                                                  70

(2) INFORMATION FOR SEQ ID NO: 216:

(i) SEQUENCE CHARACTERISTICS:
         (A) LENGTH: 30
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 216:

ACCCTCCTAG CAGCCCTCAG AGGATAGACT                                       30

(2) INFORMATION FOR SEQ ID NO: 217:

(i) SEQUENCE CHARACTERISTICS:
         (A) LENGTH: 27
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 217:

CACTGTCCCT GGTTAAACTC TACTCAG                                          27

(2) INFORMATION FOR SEQ ID NO: 218:

(i) SEQUENCE CHARACTERISTICS:
         (A) LENGTH: 67
         (B) TYPE: NUCLEIC ACID
         (C) STRANDEDNESS: SINGLE
         (D) TOPOLOGY: LINEAR (iv) ANTI-SENSE: NO (xi) SEQUENCE DESCRIPTION: SEQ ID NO: 218:

CCGCCCGCCC CGCCCGCCGC CCGCCCCGCC CGCCGCCCGC GTCAATCCTA                 50
```

GATGCTGAGC ATGTGTG                                                  67

(2) INFORMATION FOR SEQ ID NO: 219:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 219:

CCGCCCGCCC CGCCCGCCGC CCGCCCCGCC CGCCGCCCGC CATCAGGATG              50

TGGCCCCAGG CTCAGTC                                                  67

(2) INFORMATION FOR SEQ ID NO: 220:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 220:

GGCCGTTCCC CTGTCCTCCC TGCAGAT                                       27

(2) INFORMATION FOR SEQ ID NO: 221:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 221:

GGAAACTCTG GGCCAGAAGT ACCTTTG                                       27

(2) INFORMATION FOR SEQ ID NO: 222:

(i) SEQUENCE CHARACTERISTICS:
        (A) LENGTH: 30
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 222:

ATCAGCTCAG CCCACATTCA CATCTCTCAG                                    30

(2) INFORMATION FOR SEQ ID NO: 223:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 223:

CCGCCCGCCC CGCCCGCCGC CCGCCCCGCC CGCCGCCCGC CCCAGCCCCC              50

AGGGCACCTG GAGGCTG                                                  67

(2) INFORMATION FOR SEQ ID NO: 224:

(i) SEQUENCE CHARACTERISTICS:
        (A) LENGTH: 70
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 224:

```
CCGCCCGCCC CGCCCGCCGC CCGCCCCGCC CGCCGCCCGC AGTGCAGGGA          50

GGCATGCATG CACTGTCTGA                                           70
```

(2) INFORMATION FOR SEQ ID NO: 225:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 225:

```
TATGGCAAAG GACTGACACA GAGAGCCTG                                 29
```

(2) INFORMATION FOR SEQ ID NO: 226:

(i) SEQUENCE CHARACTERISTICS:
        (A) LENGTH: 64
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 226:

```
CCGCCCGCCC CGCCCGCCGC CCGCCCCGCC CGCCGCCCGC TTCCCTGCAC          50

CCCTGGCTGT CACT                                                 64
```

(2) INFORMATION FOR SEQ ID NO: 227:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 227:

```
TGGAGGCTGG GACATGGGTC CAGA                                      24
```

(2) INFORMATION FOR SEQ ID NO: 228:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 228:

```
CATGTCCCAG CCTCCACAGA TGACACAAT                                 29
```

(2) INFORMATION FOR SEQ ID NO: 229:

(i) SEQUENCE CHARACTERISTICS:
        (A) LENGTH: 72
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 229:

```
CCGCCCGCCC CGCCCGCCGC CCGCCCCGCC CGCCGCCCGC GGCCCAAGGA          50

GGCAGCCCGC ATTGGCCAAC AG                                        72
```

(2) INFORMATION FOR SEQ ID NO: 230:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 230:

```
CCGCCCGCCC CGCCCGCCGC CCGCCCCGCC CGCCGCCCGC CTTCTCCCCC          50

ACTGCTGTTG GTTGATCA                                             68
```

(2) INFORMATION FOR SEQ ID NO: 231:

(i) SEQUENCE CHARACTERISTICS:
        (A) LENGTH: 26
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 231:

```
TACCACGAAG ACCCCTACTG GATGCA                                    26
```

(2) INFORMATION FOR SEQ ID NO: 232:

(i) SEQUENCE CHARACTERISTICS:
        (A) LENGTH: 70
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 232:

```
CCGCCCGCCC CGCCCGCCGC CCGCCCCGCC CGCCGCCCGC TTCAGGGAGA          50

GGTGCTGTCC ACTACAGACT                                           70
```

(2) INFORMATION FOR SEQ ID NO: 233:

(i) SEQUENCE CHARACTERISTICS:
        (A) LENGTH: 31
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 233:

```
GCTCCTCAAA AAGGGCTAAC AGAAACCTTC A                              31
```

(2) INFORMATION FOR SEQ ID NO: 234:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 234:

```
CCGCCCGCCC CGCCCGCCGC CCGCCCCGCC CGCCGCCCGC ACAGCAAATT           50

CCTCTTGGGC AGGGACTG                                              68
```

(2) INFORMATION FOR SEQ ID NO: 235:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 235:

```
CAGTGGCAGA CTGCCCAGAC CCTCTCT                                    27
```

(2) INFORMATION FOR SEQ ID NO: 236:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 236:

```
CCGCCCGCCC CGCCCGCCGC CCGCCCCGCC CGCCGCCCGC GACTTCTCTG           50

TTAAAATGGG GCCAGAG                                               67
```

(2) INFORMATION FOR SEQ ID NO: 237:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 237:

```
ACAGAACCCC TTTGGCAGGA GATAAGA                                    27
```

(2) INFORMATION FOR SEQ ID NO: 238:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 238:

```
AGGGTGCGGG TATGGGCTGC ACAGTAA                                    27
```

(2) INFORMATION FOR SEQ ID NO: 239:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 239:

```
CCGCCCGCCC CGCCCGCCGC CCGCCCCGCC CGCCGCCCGC CTGCACTGAC          50

TCCCTGGCTC TCTGGTT                                              67
```

(2) INFORMATION FOR SEQ ID NO: 240:

(i) SEQUENCE CHARACTERISTICS:
        (A) LENGTH: 69
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 240:

```
CCGCCCGCCC CGCCCGCCGC CCGCCCCGCC CGCCGCCCGC TCAGGGTGAG          50

GGCTTTTGGG TTAACAGAG                                            69
```

(2) INFORMATION FOR SEQ ID NO: 241:

(i) SEQUENCE CHARACTERISTICS:
        (A) LENGTH: 29
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 241:

```
TGGATGTGGA ACTGGCCTGA GTGGAGGTA                                 29
```

(2) INFORMATION FOR SEQ ID NO: 242:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 242:

```
AGGACACACA CGCAGATACT CACAGAGT                                  28
```

(2) INFORMATION FOR SEQ ID NO: 243:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 243:

```
CCGCCCGCCC CGCCCGCCGC CCGCCCCGCC CGCCGCCCGC CAGGAGCCCT          50

TCCTTGAGGG AACAATTC                                             68
```

(2) INFORMATION FOR SEQ ID NO: 244:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 244:

CCTCTTCAGG CTGGGTTTTT AGTGCCA                                    27

(2) INFORMATION FOR SEQ ID NO: 245:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 245:

CCGCCCGCCC CGCCCGCCGC CCGCCCCGCC CGCCGCCCGC GGGGCCAGGC        50

CTCTTTGTGA GGTGCAG                                                 67

(2) INFORMATION FOR SEQ ID NO: 246:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 246:

CCCTTTCCAT ACCAGGCTCT GAGACCAC                                   28

(2) INFORMATION FOR SEQ ID NO: 247:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 247:

CCGCCCGCCC CGCCCGCCGC CCGCCCCGCC CGCCGCCCGC AGTGAAGGCC        50

AGCCTGGAGC TCTCCAGA                                               68

(2) INFORMATION FOR SEQ ID NO: 248:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 248:

CCGCCCGCCC CGCCCGCCGC CCGCCCCGCC CGCCGCCCGC TGAGGAAGGG        50

TGAGATGAGT CCTCACT                                                 67

(2) INFORMATION FOR SEQ ID NO: 249:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 249:

CTACCCCATG CTCTGTGAGC TCAGAAG                            27

(2) INFORMATION FOR SEQ ID NO: 250:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 250:

CCGCCCGCCC CGCCCGCCGC CCGCCCCGCC CGCCGCCCGC CAGACAGAGC         50

TGTGCTGAGA GGACGAAG                                         68

(2) INFORMATION FOR SEQ ID NO: 251:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 251:

AGACAAGGGA CAGTCCTGAG GGTGCTGA                          28

(2) INFORMATION FOR SEQ ID NO: 252:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 252:

GCAGGGGTGC TTACCACTTG CACTCAT                            27

(2) INFORMATION FOR SEQ ID NO: 253:

(i) SEQUENCE CHARACTERISTICS:
        (A) LENGTH: 68
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 253:

CCGCCCGCCC CGCCCGCCGC CCGCCCCGCC CGCCGCCCGC TCCTTGCTGA         50

CCCAGCACAG AGACTCAC                                         68

(2) INFORMATION FOR SEQ ID NO: 254:

(i) SEQUENCE CHARACTERISTICS:
        (A) LENGTH: 66
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 254:

```
CCGCCCGCCC CGCCCGCGCC CGCCCCGCCC GCCGCCCGCG GGCAGAAGAG          50

GAGAGGCCTG GGCTTC                                               66
```

(2) INFORMATION FOR SEQ ID NO: 255:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 255:

```
GTCCTTCTAG GCTGAGATGA GACTTGT                                   27
```

(2) INFORMATION FOR SEQ ID NO: 256:

(i) SEQUENCE CHARACTERISTICS:
        (A) LENGTH: 66
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 256:

```
CCGCCCGCCC CGCCCGCCGC CGCCCCGCC CGCCGCCCGC GGAACATTCT           50

TCTCTGAGCC TGAGAC                                               66
```

(2) INFORMATION FOR SEQ ID NO: 257:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 257:

```
CAGGGGAAGG CGGCTTTTAC TGAATTC                                   27
```

(2) INFORMATION FOR SEQ ID NO: 258:

(i) SEQUENCE CHARACTERISTICS:
        (A) LENGTH: 67
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 258:

```
CCGCCCGCCC CGCCCGCCGC CGCCCCGCC CGCCGCCCGC CTGGACTAAG          50

GAGCAGTGGC CTCAGAT                                              67
```

(2) INFORMATION FOR SEQ ID NO: 259:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 259:

CAGCCCTGAG GAAATCCTAG AAACTGC                                           27

(2) INFORMATION FOR SEQ ID NO: 260:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 260:

AATATAGATA GATATGTCTG TGCTGAC                                           27

(2) INFORMATION FOR SEQ ID NO: 261:

(i) SEQUENCE CHARACTERISTICS:
        (A) LENGTH: 66
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 261:

CCGCCCGCCC CGCCCGCCGC CCGCCCCGCC CGCCGCCCGC GGCCCCCTCC                  50

ATCTTCCAAC TCCATG                                                       66

(2) INFORMATION FOR SEQ ID NO: 262:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (xi) SEQUENCE DESCRIPTION: SEQ ID NO: 262:

CAACTCCGGC AGAACTCCG                                                    19

(2) INFORMATION FOR SEQ ID NO: 263:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 263:

TATATCTGTG CGCAAACTTC                                                   20

(2) INFORMATION FOR SEQ ID NO: 264:

(i) SEQUENCE CHARACTERISTICS:
        (A) LENGTH: 20
        (B) TYPE: NUCLEIC ACID

```
            (C) STRANDEDNESS:  SINGLE
            (D) TOPOLOGY: LINEAR (xi) SEQUENCE DESCRIPTION:  SEQ ID NO: 264:

AGAAGACGCA GAGCGCTGCT                                              20

(2) INFORMATION FOR SEQ ID NO: 265:

(i) SEQUENCE CHARACTERISTICS:
            (A) LENGTH: 19
            (B) TYPE: NUCLEIC ACID
            (C) STRANDEDNESS:  SINGLE
            (D) TOPOLOGY: LINEAR (xi) SEQUENCE DESCRIPTION:  SEQ ID NO: 265:

ACAGAGTCTT GATTGGCAG                                               19

(2) INFORMATION FOR SEQ ID NO: 266:

(i) SEQUENCE CHARACTERISTICS:
            (A) LENGTH: 22
            (B) TYPE: NUCLEIC ACID
            (C) STRANDEDNESS:  SINGLE
            (D) TOPOLOGY: LINEAR (xi) SEQUENCE DESCRIPTION:  SEQ ID NO: 266:

CTCAGCGTGC TTCATAGGAT TC                                           22

(2) INFORMATION FOR SEQ ID NO: 267:

(i) SEQUENCE CHARACTERISTICS:
            (A) LENGTH: 24
            (B) TYPE: NUCLEIC ACID
            (C) STRANDEDNESS:  SINGLE
            (D) TOPOLOGY: LINEAR (xi) SEQUENCE DESCRIPTION:  SEQ ID NO: 267:

TCTAGTGTCT CAGGCTCATT CACT                                         24

(2) INFORMATION FOR SEQ ID NO: 268:

(i) SEQUENCE CHARACTERISTICS:
            (A) LENGTH: 20
            (B) TYPE: NUCLEIC ACID
            (C) STRANDEDNESS:  SINGLE
            (D) TOPOLOGY: LINEAR (xi) SEQUENCE DESCRIPTION:  SEQ ID NO: 268:

CTGATTAGAT CTTGAGCTCT                                              20

(2) INFORMATION FOR SEQ ID NO: 269:

(i) SEQUENCE CHARACTERISTICS:
            (A) LENGTH: 20
            (B) TYPE: NUCLEIC ACID
            (C) STRANDEDNESS:  SINGLE
            (D) TOPOLOGY: LINEAR (xi) SEQUENCE DESCRIPTION:  SEQ ID NO: 269:

CTGGATTAAC ATAGCATTGC                                              20

(2) INFORMATION FOR SEQ ID NO: 270:

(i) SEQUENCE CHARACTERISTICS:
            (A) LENGTH: 20
            (B) TYPE: NUCLEIC ACID
            (C) STRANDEDNESS:  SINGLE
            (D) TOPOLOGY: LINEAR
```

(xi) SEQUENCE DESCRIPTION: SEQ ID NO: 270:

GCAATGCTAT GTTAATCCAG                                              20

(2) INFORMATION FOR SEQ ID NO: 271:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 271:

TCACCTTTGT CACCACGATC                                              20

(2) INFORMATION FOR SEQ ID NO: 272:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 272:

GCTCTCTCTC ACAGATTGTA                                              20

(2) INFORMATION FOR SEQ ID NO: 273:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (xi) SEQUENCE DESCRIPTION: SEQ ID NO: 273:

GTAAGTGCAA GCAGCAATT                                               19

(2) INFORMATION FOR SEQ ID NO: 274:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 274:

ATTGCTGCTT GCACTTACCT G                                            21

(2) INFORMATION FOR SEQ ID NO: 275:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 275:

AGCAAGAGGT TGTCAGACTC T                                            21

(2) INFORMATION FOR SEQ ID NO: 276:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 276:

```
GCAGACAGCA GCTACTGTTC T                                                    21

(2) INFORMATION FOR SEQ ID NO: 277:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 277:

ATGAGGATAC CAGGTCAATC                                                      20

(2) INFORMATION FOR SEQ ID NO: 278:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 278:

CATCGTGTCG CAGATGATTC                                                      20

(2) INFORMATION FOR SEQ ID NO: 279:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (xi) SEQUENCE DESCRIPTION: SEQ ID NO: 279:

ACAGCAGCTG CGTCCTAGT                                                       19

(2) INFORMATION FOR SEQ ID NO: 280:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 280:

GCAGACAGCA GCTACTGTTC T                                                    21

(2) INFORMATION FOR SEQ ID NO: 281:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (xi) SEQUENCE DESCRIPTION: SEQ ID NO: 281:

ACAGCAGCTG CGTCCTAGT                                                       19

(2) INFORMATION FOR SEQ ID NO: 282:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 282:

GCTTCCTCCT CCTGCTCCAA G                                                    21
```

(2) INFORMATION FOR SEQ ID NO: 283:

(i) SEQUENCE CHARACTERISTICS:
        (A) LENGTH: 17
        (B) TYPE: NUCLEIC ACID
        (C) STRANDEDNESS: SINGLE
        (D) TOPOLOGY: LINEAR (xi) SEQUENCE DESCRIPTION: SEQ ID NO: 283:

GAGACCAGGA TATCTGA                                        17

(2) INFORMATION FOR SEQ ID NO: 284:

(i) SEQUENCE CHARACTERISTICS:
        (A) LENGTH: 19
        (B) TYPE: NUCLEIC ACID
        (C) STRANDEDNESS: SINGLE
        (D) TOPOLOGY: LINEAR (xi) SEQUENCE DESCRIPTION: SEQ ID NO: 284:

GTTCAGTGGA GTCACAGGA                                      19

(2) INFORMATION FOR SEQ ID NO: 285:

(i) SEQUENCE CHARACTERISTICS:
        (A) LENGTH: 21
        (B) TYPE: NUCLEIC ACID
        (C) STRANDEDNESS: SINGLE
        (D) TOPOLOGY: LINEAR (xi) SEQUENCE DESCRIPTION: SEQ ID NO: 285:

AGTTAGAGGA GAGCACAAGG A                                  21

(2) INFORMATION FOR SEQ ID NO: 286:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (xi) SEQUENCE DESCRIPTION: SEQ ID NO: 286:

TCGACGTCGT CGTCTTAA                                      18

(2) INFORMATION FOR SEQ ID NO: 287:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 287:

CAAGTTACTG ATCTGCAGCT                                  20

(2) INFORMATION FOR SEQ ID NO: 288:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (xi) SEQUENCE DESCRIPTION: SEQ ID NO: 288:

GACAGATGGC TCTTGGAGAA                                  20

(2) INFORMATION FOR SEQ ID NO: 289:

(i) SEQUENCE CHARACTERISTICS:
       (A) LENGTH: 22
       (B) TYPE: NUCLEIC ACID
       (C) STRANDEDNESS: SINGLE
       (D) TOPOLOGY: LINEAR (xi) SEQUENCE DESCRIPTION: SEQ ID NO: 289:

CAGACTCTCT GGCTCTACTA AG                                             22

(2) INFORMATION FOR SEQ ID NO: 290:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: LINEAR (xi) SEQUENCE DESCRIPTION: SEQ ID NO: 290:

GCAGCTCTGA CTTGGCACAT                                                20

(2) INFORMATION FOR SEQ ID NO: 291:

(i) SEQUENCE CHARACTERISTICS:
       (A) LENGTH: 18
       (B) TYPE: NUCLEIC ACID
       (C) STRANDEDNESS: SINGLE
       (D) TOPOLOGY: LINEAR (xi) SEQUENCE DESCRIPTION: SEQ ID NO: 291:

ATCATCTGCG ACACGATG                                                  18

(2) INFORMATION FOR SEQ ID NO: 292:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: LINEAR (xi) SEQUENCE DESCRIPTION: SEQ ID NO: 292:

GTGGTCTATC ATTAGAGGCT                                                20

(2) INFORMATION FOR SEQ ID NO: 293:

(i) SEQUENCE CHARACTERISTICS:
       (A) LENGTH: 20
       (B) TYPE: NUCLEIC ACID
       (C) STRANDEDNESS: SINGLE
       (D) TOPOLOGY: LINEAR (xi) SEQUENCE DESCRIPTION: SEQ ID NO: 293:

CATCGTGTCG CAGATGATTC                                                20

PRIMERS AND METHODS FOR DETECTING MUTATIONS IN THE PROCOLLAGEN II GENE (COL2A1) THAT INDICATE A GENETIC PREDISPOSITION FOR A COL2A1-ASSOCIATED DISEASE

CROSS REFERENCE TO RELATED APPLICATIONS

This application claims priority pursuant to 35 U.S.C. §363 to PCT Application No. PCT/US93/10964, filed Nov. 12, 1993 and is a continuation of U.S. application Ser. No. 07/977,284, filed Nov. 13, 1992 (now U.S. Pat. No. 5,558, 988).

ACKNOWLEDGEMENT OF GOVERNMENT RIGHTS

Research for this invention was supported in part by the National Institutes of Health Grants AR-381 88 and AR-39740. The government may have certain rights in the invention.

FIELD OF INVENTION

The present invention relates to the field of compounds and methods for detecting genetic diseases linked to anomalies of genes for collagens and other structural proteins found in cartilage and joints.

BACKGROUND OF THE INVENTION

Osteoarthritis is a progressive disease of joints that is a cause of serious disability in large numbers of people. The disease is defined as a progressive degeneration of the cartilaginous surfaces of joints that leads to stiffness, pain, and loss of mobility. Degeneration of the cartilaginous surface of joints seen in osteoarthritis can have a number of causes. For example, severe trauma to a joint or a bacterial infection in a joint can produce degeneration of the joint that is either immediate or slowly progressive over many years. A number of metabolic disturbances are also know to produce degeneration of joints.

Cartilage and membranes that line joints are complex structures. A major source of the strength of cartilage is the fibrils of type II collagen. The fibrils of type II collagen are stretched into three-dimensional arcades primarily by the presence of another group of macromolecules called proteoglycans. Proteoglycans are highly charged and, therefore, absorb water and salts and thereby extend the arcades of type II collagen fibrils. As a result, a highly resilient structure is formed that can withstand the intermittent pounding and pressures that joints must undergo. In addition to proteoglycans and type II collagen, cartilage is known to contain at least four other kinds of collagens (types VI, IX, X and XI) in lesser amounts than type II collagen. It is very likely that additional collagens will be discovered in cartilage in the future. In addition, it is clear that the matrix of cartilage also contains a number of other proteins that are still poorly characterized and that may contribute to the structure and function of the tissue.

Collagens, proteoglycans and other proteins found in the matrix of cartilage are synthesized by cells embedded within the matrix. The matrix is actively synthesized during embryonic development of certain tissues and during periods of growth. The rates of synthesis and degradation of the matrix are less during adult life. However, throughout life, a continual slow synthesis and degradation of cartilage occurs, particularly in response to the pressures associated with physical activity.

Cartilage itself has several different functions in the body. During embryonic development, transient tracks of type II collagen and probably other components of cartilage are formed in many structures. The tracks appear to serve as a guide for cell migration and a template for formatting of skeleton and associated structures. in addition, cartilage serves as a precursor structure for many bones. During the development of long bones such as those of the arms and legs, cartilage is part of the growth plate in which cell growth occurs. More specifically, the cartilage grows away from the midpoint of the long bone and is continually degraded and gradually replaced by bone itself. An additional function of cartilage is to give shape and form to tissues such as the nose and ears. Many of the macromolecules found in cartilage are also present in the vitreous gel of the eye and account for the high viscosity of the vitreous. Still another major function of cartilage is to provide strength and resilience to structures such as the intervertebral disc of the spine. In joints, it provides not only strength and resilience, but also the smooth surfaces for motion under heavy loads.

The degeneration of joint cartilages that occurs in osteoarthritis is caused by a failure of the cartilage to maintain its structural integrity. In this process, the cartilage surface is eroded by physical pressures and is not adequately replaced by the new synthesis of cartilage. Instead of adequate repair of cartilage, secondary changes occur in the joint surface and in the joint. These changes include, for example, inflammatory responses characterized by invasion of white cells and macrophages, abnormal deposition of mineral in the form of calcium and phosphate within the joint space and in the cartilage itself, deposition of fibers of type I and other collagens that are not normally part of cartilage or the joint, abnormal growth of cartilage cells and matrix at locations adjacent to the joint surface and abnormal calcifications of the joints and associated structures. As part of the complex changes that occur, the cells of the cartilage or the invading cells from the blood stream begin to secrete degradative enzymes that further contribute to the degradation of the joint structures.

In the more severe diseases of cartilage known as chondrodysplasias, serious defects in the formation of cartilage are apparent early in life and there is a failure of joints to develop their normal size and shape. There is also a secondary failure of bone growth seen in these diseases. Moreover, there can be a failure of normal development of many tissues such as failure to achieve closure of normal partitions between oral and nasal passages, known as cleft palate, and improper development of the vitreous gel of the eye that causes severe myopia and retinal detachment.

Research has demonstrated that some forms of osteoarthritis and related conditions are caused by mutations in the genes that code for and, therefore, determine the structure of the collagens that are the major source of the strength of cartilage. Mutations of collagen that have been defined include, for example, mutations in the gene for type II collagen and its precursor type II procollagen. These mutations are of two general kinds. One kind of mutation decreases the synthesis of type II procollagen. The second kind of mutation leads to the synthesis of a defective form of type II procollagen. As a result of these mutations, there is either a decrease in the normal level of type II collagen in cartilage and other tissues that contain the protein or the formation of abnormal type II collagen fibrils that do not have the strength of normal type II collagen fibrils and, therefore, cause the cartilage of joints to be degraded by normal wear and tear. The two kinds of mutations can also produce drastic effects during normal growth and development. As a result, some individuals who inherit some of the mutated genes develop severe chondrodysplasias and die in utero or shortly after birth. Alternatively, such individuals can have serious deformities such as dwarfism which shows severe malformation of joints and may be associated with conditions of severe myopia, myopia with retinal detachment and blindness, cataracts, cleft palate, and unusual facial appearance. Other similar mutations in the same genes may produce much milder effects and cause progressive generalized osteoarthritis in which affected individuals are apparently normal until middle age when they develop progressive stiffness, pain and then immobility of many joints. Mutations of the gene for type II procollagen and collagen have been shown to cause these disorders. Research suggests that some of the conditions are caused by similar mutations in other genes that code for other structural macromolecules found in cartilage which contribute to its normal resistance to wear and tear. Methods and compounds are therefore desired for the analysis and detection of mutations in genes, both for type II procollagen and for a series of known collagens that are components of cartilage (types VI, IX, X and XI), as well as for still undiscovered collagens and other structural proteins that contribute to the normal strength and function of cartilage.

SUMMARY OF THE INVENTION

The invention provides probes and primers complementary to certain regions of collagen genes. Also provided are methods using such primers and probes for detecting mutations in a collagen gene sequence isolated from cells from individuals suspected of exhibiting mutant collagen gene expression or containing mutant collagen genes. Also included are methods to detect mutations in the collagen genes of members of the individual's family.

More specifically, the invention provides a method whereby an individual who has developed osteoarthritis or a related condition, or is suspected of developing osteoarthritis or a related condition, is tested to see if the individual has a mutation in the DNA of a gene for a structural protein that is a normal component of cartilage. This method provides that the DNA sequence of a collagen gene is examined in an individual with osteoarthritis or a related condition. The DNA sequence is also compared with corresponding regions of a standard DNA from a series of individuals known not to have the disease in question. Any difference in the base sequence from the DNA of the individual tested as compared to the standard sequence is then evaluated in terms of whether or not it indicates an increased likelihood of the individual suffering from osteoarthritis or related disorder. For the first member of a family tested, all or a substantial portion of DNA coding for the gene is sequenced and compared to the standard sequence.

The invention also provides that once the location of the gene mutation causing the disease is known, it can be looked for in members of the first individual's family. For each genetically predisposed individual family member, the mutation in the gene is expected to appear in the same position in the collagen gene tested. A difference in base sequence of the DNA from the individual tested as compared with the standard sequence can be evaluated to determine how the mutation will effect expression of the gene. The potential for the difference in DNA sequence to produce the disease can also be evaluated in terms of whether it changes an amino acid sequence that is critical for the normal functioning of the protein.

Methods further provide that DNA derived from the cells of the test sample is analyzed to determine whether or not the collagen gene contains a mutation. If a mutation is found in the gene, a rapid test can be devised for other members of the patient's family to determine whether or not they have the same mutation.

The methods of the invention are particularly useful in detecting mutations in human collagen genes. It is believed that these methods will also be useful in detecting mutant collagen genes in mammals.

Intronic sequences provided by the invention are useful for developing oligonucleotide primers to amplify and sequence genomic DNA from patients suspected of having mutations in the gene for the proαI (II) chain of type II procollagen which cause various disorders.

Methods of the present invention for detecting mutations in the gene for type II procollagen can readily be applied to detection of mutations in genes coding for other structural proteins found in cartilage and associated tissues. For example, the nucleotide sequences of these genes can be used to design oligonucleotide primers to amplify genomic DNA or cDNA for the gene. The products obtained using PCR can then be used to define the base sequences of genomic DNA or cDNA. Mutations in the genes for these other collagens and structural proteins in matrix that cause osteoarthritis and related conditions can be detected in the same manner as mutations in the gene for type II procollagen.

DETAILED DESCRIPTION OF THE INVENTION

Figure 1:
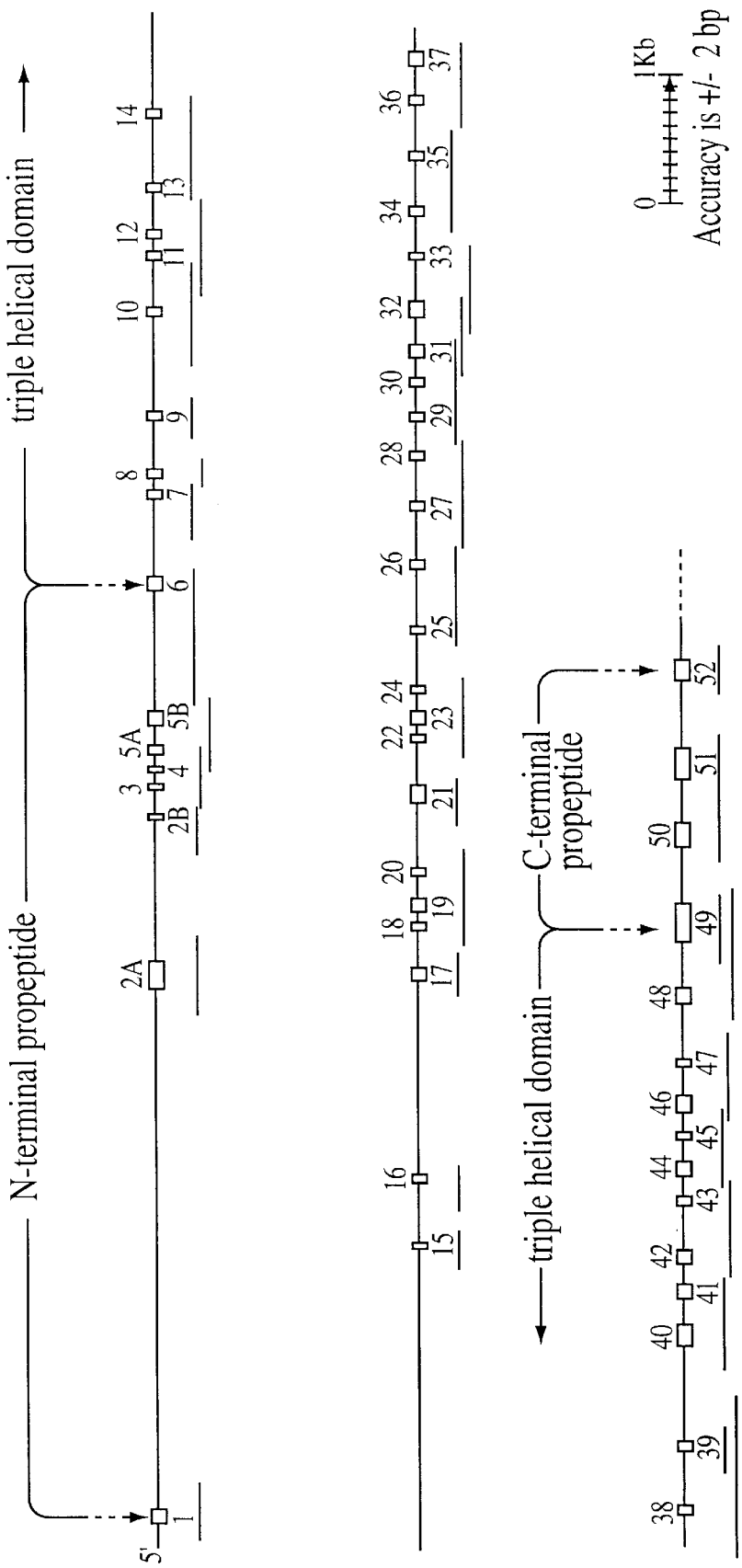
FIG. 1 shows a gene map of type II procollagen (COL2A1) with introns and exons designated by lines and crosshatched boxes respectively.

The present invention concerns methods of diagnosing specific kinds of osteoarthritis in which there is systemic degeneration of many joints without any apparent external cause. In particular, the invention relates to progressive generalized osteoarthritis that produces degeneration of the cartilage of many joints. It also concerns diseases in which there is malformation of joints that is apparent at birth or during childhood and that leads to progressive degeneration of joints, as well as other symptoms such as dwarfism and severe malformation of the skeleton and other cartilaginous tissues. More particularly, the invention is directed to diagnosing diseases characterized by degeneration of joints in which the presence of the disease in several members of the same family or similarity between the disease of a given patient and diseases seen in families indicates that the disease has a genetic origin. Therefore, the invention concerns not only progressive generalized osteoarthritis, but also a group of related disorders that are generally defined as chondrodysplasias. Skeletal dysplasia or related disease involving abnormalities of growth and of cartilaginous structures and of tissues containing the same structural proteins as cartilage including chrondrodysplasias, epiphyseal dysplasia, metaphyseal dysplasia, spondyloepiphyseal dysplasia, spondylometaphyseal dysplasia and arthroophthalmopathy (the Wagner-Stickler syndrome) may be diagnosed using the methods of the invention. Skeletal disorders such as scoliosis and related conditions involving abnormalities in the cartilage and other components of the vertebrae column and back may also be diagnosed in accordance with the invention.

More specifically, the present invention provides methods for gene analysis whereby one can definitively establish the cause of osteoarthritis and of chondrodysplasias in individuals and in members of the individuals' families. Such methods will make it possible to identify individuals in families who are predisposed to develop these diseases. In the case of severe chondrodysplasias that produce crippling deformities and that may even be lethal, such methods will be useful for prenatal diagnosis. In the case of milder chondrodysplasias and osteoarthritis, the results of the gene analyses may be used to counsel individuals predisposed to develop the diseases concerning preventive exercise programs, life styles, choice of careers, and family planning. Also, the information generated by the gene analyses using the methods of the present invention may be used to develop new rational therapies for diseases of collagen. Moreover, the information can be used to develop animal models for such diseases. For example, information may be useful to develop transgenic mice that will provide new means of testing new agents to cure and prevent the diseases.

Methods of the invention provide that an individual who has developed osteoarthritis or a related condition or is suspected of developing osteoarthritis or a related condition, is tested to see a if mutation in the DNA of a gene for a structural protein for example, type II procollagen, is present. The methods of the invention further provide that after a mutation causing the disease or diseases in one individual is found, it can be sought in members of the first individual's family.

The gene COL2A1 which encodes the proαI (II) chain of type II procollagen is provided and examined as a demonstration of the methods of the present invention. This demonstration in no way limits the scope of the claimed invention. In the first stage of the methods of the invention, the DNA sequence of the COL2A1 gene is examined in an individual with a cartilage and joint disease such as osteoarthritis. This DNA sequence is compared with corresponding regions of a standard DNA from a series of individuals known not to have the disease in question. It is believed that this strategy will be useful for any disease of collagen which exhibits at least one mutation in a collagen gene of the diseased mammal. The DNA sequences of the genes tested can be genomic DNA or cDNA prepared from RNA derived from a sample of cells or tissues taken from the individual. DNA may also be extracted from bodily fluids containing lysed cells. The standard DNA sequence and structure of the COL2A1 gene can be obtained by reference to known sequences or those set forth herein in FIG. 1 and listed in the literature or computerized data banks. Sequences of other collagen genes used in the methods of the present invention may also be obtained from databases or may be sequenced employing commonly used methods. See, for example, Sanger et al., DNA Sequencing With Chain-Terminating Inhibitors, *Proc. Natl. Acad. Sci. USA* 1977, 74, 5463–5467. Any difference in the base sequence from the DNA of the individual tested as compared to the standard sequence is then evaluated to determine whether it indicates an increased likelihood of the individual suffering from osteoarthritis or a related disorder. For the first member of a family tested, all or a substantial portion of DNA coding for the gene is sequenced and compared to the standard sequence. Sequencing of the first family member's DNA may be achieved by DNA sequencing techniques known in the art. These methods of the present invention are useful for all collagen genes.

As used herein, the term "collagen" includes procollagens and collagens types I to XVI, still undiscovered collagens similar to types I to XVI, and genes encoding proteins associated or comprising collagen polymers in tissue matrices.

The term "family member", as used herein, means individuals, including humans and other mammals, genetically related to one another in any degree, such as, for example, parent-child, siblings, cousins, etc. Such genetic relatedness can be determined using standard methods known in the art including, for example, pedigree analysis or DNA "fingerprinting".

Moreover, the term "individual", as used herein, denotes a mammalian individual of any species, including humans.

As illustrated by the demonstration using type II collagen, methods of detection of mutations in a collagen gene comprise several steps. One step involves selecting cells suspected of comprising a mutated collagen gene. Another step includes isolating genomic DNAs from selected cells or preparing cDNAs from selected cells. After the genomic DNA or cDNA is isolated, larger amounts of the gene sequences of interest are prepared by amplifying the DNA with the polymerase chain reaction (PCR). The DNA produced by the PCR are then analyzed for the presence of a disease-causing mutation. The preferred strategy of analysis is to first screen the PCR products with a relatively rapid technique such as denaturing gradient gel electrophoresis (DGGE) that enables one to decide whether or not a specific PCR product from one region of the gene does or does not have a mutation such as a single base difference between the two alleles of the gene. PCR products detected as probably having a mutation by such a technique are then analyzed further by a technique such as dideoxynucleotide sequencing that provides the detailed base sequence that defines the mutation. The methods comprise the aforementioned steps and further comprise comparing the sequence of the collagen gene or other genes for structural proteins of cartilage containing the mutation to corresponding regions of a family member's structural protein genes and determining if the mutation is present in the family member's genes.

It is believed that all of the methods of the present invention are useful to detect any mutation in all procollagen and collagen genes, including, for example, procollagens and collagens I to XVI, still undiscovered procollagens and collagens similar to types I to XVI, as well as other genes associated with collagen structure, such as proteoglycans. It is also believed that these methods are also useful in mammals other than humans.

A second step of the invention provides that once the location of the mutation in a gene causing the disease is known, it can be sought in members of the first individual's family. For each genetically predisposed individual family member, the mutation in the gene is expected to appear in the same position in the structural protein gene tested. For example, in Family A, the genetic mutation may be at position 30; and for Family B, the genetic mutation may be at position 505. In accordance with the methods of the invention, testing the family members can be done by comparing corresponding regions of family member's genes and determining if the mutation is present in the family member. This evaluation of a difference in base sequence of the DNA from the individual tested as compared with the standard sequence can be evaluated in terms of whether it is a disease-causing mutation by determining whether the mutation changes the level of expression of the gene in terms of the rate at which the gene is transcribed into RNA, the rate at which the initial RNA is processed into mRNA and the rate at which the mRNA can be effectively used to synthesize mature collagen matrices, such as proαI (II) chains of type II procollagen. The potential for the difference in DNA sequence to produce the disease can also be evaluated in terms of whether it changes an amino acid sequence that is critical for the normal functioning of the protein by strategies used by those familiar in the art. The strategies include demonstration that the same gene mutation is not present in individuals unaffected by the disease in the same family of the general population, detailed linkage analysis of co-inheritance of the mutation with the disease phenotype in large families or a series of families with the same mutation, and structure-function studies on the mutated protein obtained either by isolation of the protein from tissues of affected individuals or expression of the mutated gene in a recombinant system.

In accordance with the methods of the invention, DNA is extracted from a test sample of cells of the family member to be tested by conventional techniques, such as lysis of the cells with sodium dodecyl sulfate (SDS) and digestion of protein with proteinase K, followed by extraction with phenol and chloroform, and ethanol precipitation as described by Maniatis et al., *Molecular Cloning: A Laboratory Manual*, Cold Spring Harbor Laboratory, Cold Spring Harbor, N.Y., 1982, pp 280–281. A sample of cells can be taken from any type of tissues; for example, a piece of skin, a sample of blood, or by scraping of the interior of the mouth. Alternatively, mRNA can be extracted from the test sample and cDNA synthesized with reverse transcriptase, and the resulting cDNA used for analysis. Although cartilage cells cannot regularly be obtained from patients, many other cells including white blood cells have been shown to contain small amounts of the mRNAs for protein synthesized by cartilage and the mRNAs can be analyzed after conversion to cDNAs as reported by Chan and Cole, *Journal of Biological Chemistry* 1991, 266, 12487.

Following extraction, DNA derived from the cells of the test sample is analyzed to determine whether the structural protein gene contains a mutation. If a mutation is found in the gene, a rapid test can be devised for other members of the patient's family to determine whether they have the same mutation. DNA and cDNA from other structural protein genes can also be used in this method of the invention.

Although the methods of the invention have been demonstrated in the first instance in human beings, it is expected that they will be useful in other mammalian species, particularly commercially important species and in laboratory animals used as models of human disease. For example, it is believed that these methods will be particularly useful in detecting mutant collagen genes and transcripts in transgenic animals comprising mutant collagen genes or transcripts.

Some of the sequences for the normal COL2A1 gene can be found in the literature. For example, in Strom and Upholt, *Nucl. Acids Res.* 1984, 12, 1025–1038; Cheah et al., *Proc. Natl. Acad Sci. USA* 1985, 87, 2555–2559; Sangiorgi et al., *Nucl. Acids Res.* 1985, 13, 2207–2225; Nunez et al., *Gene* 1986, 44, 11–16; Su et al., *Genomics* 1989, 4, 483–441; Vikkula and Peltonen, *FEBS Lett.* 1989, 250, 171–174; Upholt, *Collagen Vol. 4*, CRC Press, Baton Rouge, Fla., 1989, pp 31–49; Ala-Kokko and Prockop, *Genomics* 1990, 8, 454–460. However, the sequences for a major part of the introns used for the synthetic oligonucleotide primers employed for the analyses described here are provided as part of the present invention. Those skilled in the art recognize that rapid analysis of a gene by these procedures requires a series of oligonucleotides that are specifically targeted to regions of the gene under analysis. However, many base sequences are not efficient targets for oligonucleotide primers. In the case of procollagen and collagen genes, the number of efficient target sites is limited by the high GC content and repetitive nature of the coding sequences. Also, most of the genes contain a large number of introns, and many of the introns are too short to offer many potential target sites (see FIG. 1). Therefore, the present invention includes efficient oligonucleotide primers for amplification of the type II procollagen gene by PCR, efficient oligonucleotide primers for analysis of PCR products of the type II procollagen gene by DGGE, and efficient oligonucleotide primers for dideoxynucleotide sequencing of PCR products of the type II procollagen. Table I presents specific oligonucleotide primers for amplification of the human type II procollagen gene by PCR and for dideoxynucleotide sequencing of the PCR products. Table II presents a series of neutral sequence variants detected in the type II procollagen gene that are important to avoid as target sites for primers, for defining haplotypes of the gene, and evaluating putative disease-causing mutations in the gene. Table III presents oligonucleotide primers that are efficient for amplifying regions of the gene by PCR in a form that makes the PCR products suitable for screening for mutations by the technique of DGGE.

The analytical methods that are part of the invention involve the PCR. One skilled in the art would recognize that there are many commonly employed schemes for amplifying nucleic acid sequences using PCR. See, for example, *PCR Protocols, A Guide to Methods and Applications*, Innis et al, Eds., Academic Press, New York, 1990, and *Current Communications, Polymerase Chain Reaction*, Ehrlich et al., Eds., Cold Spring Harbor Laboratory Press, Cold Spring Harbor, N.Y., 1989. The PCR methods of the invention for amplifying nucleic containing at least one mutation in a collagen gene comprise several steps. The steps enumerated herein are merely exemplary of the steps commonly employed by one skilled in the art performing PCR. Other steps may be added to achieve DNA amplification. Included in the invention are steps for selecting cells suspected of comprising a mutated collagen gene and isolating nucleic acid from the cells. Initial PCR steps comprise contacting the nucleic acid with a first primer and a second primer, extending the first primer to create an extension product, contacting the extension product with a second primer, and extending the second primer to create another extension product. The extension products of the first round of synthesis may be longer than the extension products of the second round of synthesis. Extension products of the first round of synthesis are contacted with the primers comprising complementary sequences. The primers used in this step may be the same primers used in the first round of synthesis. These primers are extended to form "secondary" extension products. These "secondary" extension products may be shorter than the initial extension products from which they were synthesized. Amplification steps comprise amplifying the "secondary" extension products using PCR. The initial runoff DNA extension products will be diluted during amplification. The amplification steps will favor synthesis of the "secondary" extension product DNAs having a length determined by the probes used. Once the PCR steps are completed, steps are provided for detecting the presence or absence of said mutation in at least one extension product.

It is believed that these methods will be useful for analyzing cartilage matrix protein genes, especially in humans. It is also believed that these methods are useful to analyze the matrix protein genes of other proteins found in collagen matrices, such as non-collagenous structural protein of cartilage. Further, the PCR methods of the invention are useful for determining if a mammal has a genetic predisposition for a disease exhibiting a mutant collagen gene. These methods include further steps of comparing the sequence of the collagen gene containing the mutation to corresponding regions of a family member's collagen genes and determining if the mutation is present in the family member's collagen genes. It is believed that these methods will also be useful in other mammals.

Methods of the present invention for detecting mutations in the gene for type II procollagen can readily be applied to detection of mutations in genes coding for other structural proteins found in cartilage and associated tissues. For example, the nucleotide sequences of the genes for types VI, IX, X and XI collagens can be used to design oligonucleotide primers to amplify genomic DNA or cDNA for the gene using PCR. The products obtained using PCR can then be used to define the base sequences of genomic DNA or cDNA. Therefore, mutations in the genes for these other collagens and structural proteins in matrix that cause osteoarthritis and related conditions can be detected in the same manner as mutations in the gene for type II procollagen.

The following examples are illustrative of the invention. It is understood that this invention is not limited by these illustrative examples but solely by the claims appended hereto.

EXAMPLES

Example 1

A series of procedures were developed for amplifying important regions of the gene for type II procollagen (COL2A1) by the PCR so that adequate amounts of DNA were generated for analysis. A further series of procedures made it possible to directly analyze the DNA produced by the PCR and define its base sequences.

FIG. 1 presents a diagram of the human COL2A1 gene indicating the location of the 54 exons of the gene. The figure also indicates, using short horizontal lines, the regions of the genes that were amplified with the use of appropriate oligonucleotide primers and conditioned for amplification of the gene by PCR. Table I presents the sequencing and location of the oligonucleotide primers defined by the specific base sequences of the gene beginning with number 1 at the 5'-end of the gene. Ala-Kokko and Prockop, *Genomics* 1990, 8, 454–460, disclosed all the coding sequences of the COL2A1 gene but no more than 40 intronic bases immediately flanking most of the introns.

Examples of primers effective for amplification of sequences by PCR and sequencing of the PCR products presented in Table I are within regions of the introns which have not been disclosed previously. These sequences and primers are included in the present invention. The steps whereby genomic DNA from an individual from sources such as white blood cells or any other cells in the body can be used in the procedure to detect variations in sequences are as follows. The DNA template is amplified using PCR. The PCR products can be loaded directly on an agarose gel and electrophoresed and analyzed or they can be diluted and subjected to a second round of PCR amplification. PCR products obtained from the first PCR reaction in which the regions of the gene symmetrically amplified were examined by electrophoresis in an agarose gel stained with ethidium bromide. The conditions of the experiment were adequate to generate an intense single band of DNA, an observation indicating that the target region was selectively amplified. If a second PCR amplification is carried out, the products are purified and sequenced. The second PCR in which the product of the first PCR is asymmetrically amplified generates a single-stranded DNA which can be directly used for sequencing. The results indicate the presence of two major bands of DNA, one double-stranded DNA and the second single-stranded DNA appropriate for sequencing. Analysis of the base sequences of PCR products from the second asymmetric PCR were analyzed by dideoxynucleotide sequencing using methods known in the art. The sequencing autoradiograms were of high enough quality to be able to detect single-base variations in which one allele of the gene has one base and the same position of the second allele from the same gene has a different base. For example, patients 1 and 5 had an A in one allele and a T in the other allele at position +5 of intron 9 of the COL2A1 gene, whereas patients 2, 3, and 4 had only a T in this position. Moreover, patient 4 had an A and a G in position +45 of intron 9, whereas the other patients had only a G. Similarly, DNA from one patient showed both a C and a T at position –47 of intron 26 of the COL2A1 gene, whereas a different patient had a C at this position and the patient in the right-hand four lanes had a T in this position. These results demonstrate that the procedures outlined here are adequate to detect single-base variations in a single allele.

TABLE I

Synthetic Oligonucleotide Primers for Amplification of the Type II Procollagen Gene by PCR and Sequencing of the PCR Products

| Primer Name/# | Alt. Code | Region/ Exon | Primer type | PCR/SEQ direction | Primer Position | Sequence | SEQ ID NO |
|---|---|---|---|---|---|---|---|
|  |  | 1 | PCR | sense |  |  |  |
|  |  | 1 | PCR | antisense |  |  |  |
| NA46 |  | 1 | Seq | sense |  |  |  |
| NA36 |  | 2B/5B | PCR | sense |  |  |  |
| NA10B |  | 2B/5B | PCR | antisense |  |  |  |
| NA37 |  | 2B | PCR | antisense |  |  |  |
| NA39 |  | 2B | Seq | sense |  |  |  |
| NA24 |  | 3/4 | PCR | sense |  |  |  |
| NA23 |  | 3/4 | PCR | antisense |  |  |  |
| NA28 |  | 3 | Seq | antisense |  |  |  |
| NA25A |  | 4 | Seq | sense |  |  |  |

TABLE I-continued

Synthetic Oligonucleotide Primers for Amplification of the Type II Procollagen Gene by PCR and Sequencing of the PCR Products

| Primer Name/# | Alt. Code | Region/ Exon | Primer type | PCR/SEQ direction | Primer Position | Sequence | SEQ ID NO |
|---|---|---|---|---|---|---|---|
| NA9 | | 5A/5B | PCR | sense | | | |
| CW-2 | | 5B | PCR | antisense | 7688 | tgcctaatatgtgactcttc (20) | 1 |
| NA44 | | 5A | Seq | antisense | | | |
| NA33 | | 5 | Seq | sense | | | |
| NA11A | | 5A | Seq | sense | | | |
| NA14 | | 6 | PCR | sense | | | |
| NA15 | | 6 | PCR | antisense | | | |
| NA19 | | 6 | Seq | antisense | | | |
| NA31 | | 7 | PCR | sense | | | |
| NA32 | | 7 | PCR | antisense | | | |
| NA20 | | 7 | Seq | antisense | | | |
| NA40 | | 7 | Seq | sense | | | |
| NA17 | | 8 | PCR/Seq | antisense | | | |
| NA18 | | 8 | PCR | antisense | | | |
| NA21 | | 8 | Seq | antisense | | | |
| 23 | DH-15 | 9 | PCR | sense | 281 | agcctgtgctatctgctgcaat (22) | 2 |
| 22 | DH-14 | 9 | PCR | sense | 300 | aatcccactatgatctctgc (20) | 3 |
| 24 | DH-16 | 9 | Seq | sense | 395 | tccattgcttaggtgt (16) | 4 |
| 25 | DH-17 | 9 | PCR | antisense | 629 | cagtcttgctcctcaagatac (21) | 5 |
| 1 | | 10 | PCR | sense | 900 | caggatgtctacaaaggatgc (21) | 6 |
| 2 | | 10 | Seq | sense | 1081 | ttgcccatggcgtatg (16) | 7 |
| 99 | | 10 | Seq | sense | 1169 | catgagtgagccggtacagaag (22) | 8 |
| 3 | | 10 | PCR | antisense | 1703 | caaagtggaggtgttcagag (20) | 9 |
| 4 | | 11/12 | PCR | sense | 1424 | gtcacttctgagatgaaacgcc (22) | 10 |
| 5 | | 11 | Seq | sense | 1583 | agctgtccaagtgtg (15) | 11 |
| 100 | | 11 | Seq | sense | 1590 | caagtgtgggattcgagacaac (23) | 12 |
| CW-14 | | 11 | Seq | sense | 1640 | cctcctgcagccagggca (18) | 13 |
| 102 | | 12 | Seq | sense | 1770 | gtatcacgggtgagaag (17) | 14 |
| 12 | | 12 | Seq | sense | 1771 | tatcacgggtgagaag (16) | 15 |
| 101 | | 12 | Seq | sense | 1824 | ctttggggtgcgtgcatttc (20) | 16 |
| 6 | | 12 | Seq | sense | 1849 | acttgggtttcccag (15) | 17 |
| CW-11 | | 11 | PCR | antisense | 1875 | tcaatcagacttctgggaaacc (22) | 18 |
| 7 | | 11/12 | PCR | antisense | 2166 | tcagctcgcactgacacaaac (21) | 19 |
| 8&8A | | 13/14 | PCR | sense | 2142 | tgaagtttgtgtcagtgcgagc (22) | 20 |
| 103 | | 13 | Seq | sense | 2165 | gagatgaccagggcttttg (19) | 21 |
| 9 | | 13 | Seq | sense | 2168 | atgaccagggcttttg (16) | 22 |
| 104 | | 14 | Seq | sense | 2689 | catcaggaggtccttg (16) | 23 |
| 105 | | 14 | Seq | sense | 2725 | ctccctctcctctggtatc (19) | 24 |
| 10 | | 14 | Seq | sense | 2794 | ctcatgcttaggctg (15) | 25 |
| 11 | | 13/14 | PCR | antisense | 2927 | ctaaagtgctcggcaaatggtg (22) | 26 |
| 13 | | 14 | Seq | sense | ? | atcaggaggtccttg (15) | 27 |
| 26 | | 15 | PCR | sense | 5780 | tcgcacagacaccaaaactgca (22) | 28 |
| 27 | | 15 | Seq | sense | 5843 | caggcacagtgtgtccttcgt (21) | 29 |
| 28 | | 15 | PCR | antisense | 6070 | atacaccctcgagactgccttg (22) | 30 |
| 29 | | 15 | PCR | antisense | 6110 | ctttccagtagacatcagagtg (22) | 31 |
| 30 | DH-22 | 16 | PCR | sense | 6241 | cttctcaccacagatgtagtca (22) | 32 |
| 32 | DH-24 | 16 | PCR | sense | 6354 | gatatggagtgaaatcagtac (21) | 33 |
| 31 | DH-23 | 16 | PCR | sense | 6361 | agtgaaatcagtacaga (17) | 34 |
| 33 | DH-25 | 16 | PCR | antisense | 6609 | gttgttgagggagcaatgagcaag (24) | 35 |
| 34 | DH-26 | 16 | PCR | antisense | 6704 | caggtgagactgcgagtgtctg (22) | 36 |
| 35 | | 17 | PCR | sense | 7879 | aactgtgtgtgaaccgacatgttc (24) | 37 |
| 36 | | 17 | Seq | sense | 7920 | catgtgcataatttagtgctgt (22) | 38 |
| CW-3 | | 17/19 | PCR | sense | 7934 | agtgctgtcgttgcagctgg (20) | 39 |
| 37 | | 17 | PCR | antisense | 8217 | cacaactgtcagagcaaagtac (22) | 40 |
| 38 | DH-30 | 17 | PCR | antisense | 8244 | cagaatgaaggtttggtggttg (22) | 41 |
| 39 | DH-31 | 18/19 | PCR | sense | 8296 | cttgaaacacatagtgggaatgtc (24) | 42 |
| 40 | DH-32 | 18 | Seq | sense | 8321 | ctgaaatggacagcacctatg (21) | 43 |
| CW-5 | | 18 | Seq | sense | 8351 | tggatctggatcctggag (18) | 44 |
| 41 | DH-33 | 19 | Seq | sense | 8485 | cgtggactttgctac (15) | 45 |
| CW-1 | | 19 | Seq | sense | 8505 | gagagcccagtcctgcct (18) | 46 |
| 42 | DH-34 | 18/19 | PCR | antisense | 8710 | gactccagagatgtcagtggaac (23) | 47 |
| 43 | DH-38 | 18/19 | PCR | antisense | 8838 | caggtcctcacaccagattctctc (24) | 48 |
| 44 | DH-36 | 20 | CPR | sense | 8688 | gttccactgacatctctggagtca (24) | 49 |
| 45 | DH-37 | 20 | Seq | sense | 8725 | ctctttcccatgctctc (17) | 50 |
| 46 | DH-38 | 20 | PCR | antisense | 8961 | ctgtgcctcatagaacagcag (21) | 51 |
| 47 | DH-39 | 20 | PCR | antisense | 9033 | cataatctgaaaggacccagattg (24) | 52 |
| 48 | DH-40 | 20 | PCR | antisense | ? | gttaagtctcctccaggcataatc (24) | 53 |
| 49 | DH-41 | 20 | PCR | antisense | 9212 | gaagctgtatctgggccttctca (23) | 54 |
| 50 | DH-42 | 21 | PCR | sense | 9238 | gtgaacagttggatcttag (20) | 55 |
| 51 | DH-43 | 21 | PCR | sense | 9294 | ctttatggcctctcgtcctcaag (23) | 56 |
| CW-5 | | 21/24 | PCR | sense | 9330 | ctgaaacagttgccaaggctac (22) | 57 |

TABLE I-continued

Synthetic Oligonucleotide Primers for Amplification of the Type II Procollagen Gene by PCR and Sequencing of the PCR Products

| Primer Name/# | Alt. Code | Region/ Exon | Primer type | PCR/SEQ direction | Primer Position | Sequence | | SEQ ID NO |
|---|---|---|---|---|---|---|---|---|
| 52 | DH-44 | 21 | Seq | sense | 9336 | cagttgccaaggctacttc | (19) | 58 |
| 53 | DH-45 | 21 | Seq | sense | 9355 | cttcatactctagatc | (16) | 59 |
| CW-8 | | 21 | Seq | sense | 9380 | tccaaggccaggtgaagg | (18) | 60 |
| 54 | DH-46 | 21 | PCR | antisense | 9617 | cagaacacggaccacaaggact | (22) | 61 |
| 55 | DH-47 | 21 | PCR | antisense | 9660 | gagaaagaggaggatgacatg | (21) | 62 |
| IH-1 | | 24 | PCR | sense | 9729 | gtctgagctccttcccaggaa | (21) | 63 |
| 106 | | 22/24 | PCR | sense | 9763 | cagaagttaacctctgagaatc | (22) | 64 |
| | | 22 | Seq | sense | | | | |
| CW-9 | | 22 | Seq | sense | 9768 | gttaacctctgagaatcctg | (20) | 65 |
| 107 | | 22 | Seq | sense | 9817 | gttggtgggttagtgggatg | (20) | 66 |
| CW-10 | | 23 | Seq | sense | 9929 | caggtcaagatggtctgg | (18) | 67 |
| 108 | | 23 | Seq | sense | 9960 | gagtgggagaagaggggctg | (20) | 68 |
| 109 | | 24 | Seq | sense | 10165 | cttggcttcagaccctcag | (19) | 69 |
| IH-2B | | 24 | Seq | sense | 10199 | ctccttccagccctgcactg | (20) | 70 |
| CW-7 | | 21/24 | PCR | antisense | 10350 | ctcagaggatagacttac | (18) | 71 |
| 110 | | 24 | PCR | antisense | 10404 | catctctcttttcccttgcttc | (22) | 72 |
| 111 | | | | | | | | |
| 112 | | | | | | | | |
| IH-3 | | 24 | PCR | antisense | 10423 | gcctccctaacccaaactccatct | (24) | 73 |
| IH-7 | | 25/26 | PCR | sense | 10651 | tagatgctgagcatgtgtgg | (20) | 74 |
| IH-8A | | 25 | Seq | sense | 10703 | cttagtggatgttgggtggat | (21) | 75 |
| IH-8B | | 26 | Seq | sense | 11157 | ttggctgtccatcaggatgt | (20) | 76 |
| IH-9 | | 25/26 | PCR | antisense | 11434 | gatcaacactcaatactgagg | (21) | 77 |
| PB10 | | 27/28 | PCR | sense | 11428 | gttgatctctgtggctagac | (20) | 78 |
| PB10A | | 27/28 | PCR | sense | 11532 | gcttccatgctgagaacagc | (20) | 79 |
| IH-11A | * | 27 | Seq | sense | 11588 | gtgtggaaatggagctcagc | (20) | 80 |
| PB4 | | 27 | Seq | antisense | 11900 | tctggtgtatcagctcagcc | (20) | 81 |
| 1H-11B | * | 28 | Seq | sense | 12005 | tgagtggtgcaggaagacgc | (20) | 82 |
| 1H-12 | | 28 | Seq | antisense | 12241 | accgatagtgccaagaaagctgc | (23) | 83 |
| PB12A | | 27/28 | PCR | antisense | 12295 | gctcgatgcctggacactgc | (20) | 84 |
| PB12-A1 | | 27/28 | PCR | antisense | 12413 | cgaagtgaccaagcgttagca | (21) | 85 |
| IH-10 | * | 27/28 | PCR | sense | 7 | cctcagtattgagtgttgatc | (21) | 86 |
| 91 | | 29/31 | PCR | sense | 12233 | ctggacagcagcaggcactatc | (22) | 87 |
| 92 | | 29 | Seq | sense | 12266 | cacacctcttgcagtgtccag | (21) | 88 |
| CW-12 | | 29/31 | PCR | sense | 12313 | ctgtcactgctgctgcttcc | (20) | 89 |
| 17 | | 29/31 | PCR | sense | 12341 | ggtctgccctatactgt | (17) | 90 |
| 93 | | 29 | Seq | sense | 12341 | ggtctgccctatactgtg | (18) | 91 |
| 19 | | 29 | Seq | sense | 12375 | ggcagcaaactcactc | (16) | 92 |
| 18 | | 29/31 | PCR | antisense | ? | gactccaggctaccacgaa | (19) | 93 |
| 95 | | 30 | Seq | sense | 12624 | catggaggagtgatattc | (18) | 94 |
| 94 | | 30 | Seq | sense | 12646 | ctgctgtgggagaattgttc | (19) | 95 |
| 20 | | 30 | Seq | sense | 12647 | tgctgtgggagaattgttc | (18) | 96 |
| 97 | | 31 | Seq | sense | 12779 | caatgcgggctgcctccttg | (20) | 97 |
| | | 31/32 | PCR | sense | | | | |
| 14 | | 31 | PCR | sense | 12781 | aatgcgggctgcctcctt | (18) | 98 |
| 96 | | 31 | Seq | sense | 12824 | tgctcctttcccacctc | (18) | 99 |
| 16 | | 31 | Seq | sense | 12842 | tgctcctttcccacct | (17) | 100 |
| 21 | | 31 | Seq | sense | 12842 | ctgcttctccctggacct | (18) | 101 |
| 98 | | 29/31 | PCR | antisense | 13054 | gactccaggctaccacgaag | (20) | 102 |
| CW-13 | | 20/31 | PCR | antisense | 13306 | ccaggcattccctgaagacc | (20) | 103 |
| 15 | | 31 | PCR | antisense | 13390 | agccacagctttggtga | (17) | 104 |
| IH-16-1 | | 32/33 | PCR | sense | 13076 | cgggctcaggaggaatgaag | (20) | 105 |
| IH-16 | * | 32/33 | PCR | sense | 13089 | aggaatgaagaagaacagaagtg | (23) | 106 |
| IH-17-A | * | 32 | Seq | sense | 13163 | ctggttacccaggctccatg | (20) | 107 |
| IH-17-B-1 | | 33 | Seq | sense | 13442 | tgatgaaggtttctgttagc | (20) | 108 |
| PB-17-B-2 | | 32 | Seq | antisense | 13447 | tcatcaccaggtgccataag | (20) | 109 |
| IH-18 | | 32/33 | PCR | antisense | 13786 | gatcctaatgcccagcagt | (19) | 110 |
| IH-19 | | 34/35 | PCR | sense | 13774 | gctgggcattaggatccagc | (20) | 111 |
| IH-19-C | | 34/35 | PCR | sense | 13801 | gtctgggcagtctgccactg | (20) | 112 |
| PB-20-A | * | 34 | Seq | sense | 13852 | gcaactgcagggacttctct | (20) | 113 |
| PB-20-B | | 35 | Seq | sense | 14298 | gctgcacagtaacacaggct | (20) | 114 |
| IH-21 | * | 34/35 | PCR | antisense | 14557 | actgactccctggctctctg | (20) | 115 |
| IH-21-C | | 34/35 | PCR | antisense | 14724 | gcaggcagaggctctgttaa | (20) | 116 |
| PB-22 | | 36/37 | PCR | sense | 14663 | gcacgtcactcccatcatgt | (20) | 117 |
| IH-22 | * | 36/37 | PCR | sense | 14705 | ttaacagagcctctgcctgc | (20) | 118 |
| IH-23-A | | 36 | Seq | sense | 14805 | agcagaagcaggtccaggcag | (20) | 119 |
| PB-23-B | | 37 | Seq | sense | 15079 | cgcagatactcacagagtct | (20) | 120 |
| IH-24 | | 36/37 | PCR | antisense | 15375 | ctgcgaaccatcctctgcgc | (20) | 121 |
| PB-24 | | 36/37 | PCR | antisense | 15505 | caggagatcagcagcttggt | (20) | 122 |
| PB-25 | | 38/39 | PCR | sense | 15483 | accaagctgctgatctcctg | (20) | 123 |
| IH-25 | | 38/39 | PCR | sense | 15653 | tttagtgccaagaaagctgc | (20) | 124 |

TABLE I-continued

Synthetic Oligonucleotide Primers for Amplification of the Type II Procollagen Gene by PCR and Sequencing of the PCR Products

| Primer Name/# | Alt. Code | Region/ Exon | Primer type | PCR/SEQ direction | Primer Position | Sequence | SEQ ID NO |
|---|---|---|---|---|---|---|---|
| IH-26-A | | 38 | Seq | sense | 15708 | acagaagcccaccgtcttcc (20) | 125 |
| 56 | | 39 | PCR | sense | 16081 | acagcctgtgcctgcttctatg (22) | 126 |
| 57 | | 39 | PCR | sense | 16086 | ctgtgcctgcttctatgaccaga (23) | 127 |
| 58 | | 39 | PCR | sense | 16165 | ctttccataccaggctctgaga (22) | 128 |
| PB-26-B | | 39 | Seq | sense | 16168 | tccataccaggctctgagac (20) | 129 |
| 59 | | 39 | PCR | sense | 16170 | cataccaggctctgaga (17) | 130 |
| 60 | | 39 | PCR | antisense | 16430 | gaacggactcagaggagtgaag (22) | 131 |
| PB-27 | | 38/39 | PCR | antisense | 16457 | tcagttagctactcctccag (20) | 132 |
| IH-27 | | 38/39 | PCR | antisense | 16700 | ccagtgagttcatcaccact (20) | 133 |
| 61 | DH-53 | 40/41 | PCR | sense | 16880 | tgtctcacatggtgagaaggttg (23) | 134 |
| 62 | DH-54 | 40/41 | PCR | sense | 16969 | cagagaggaaactgctgtcact (22) | 135 |
| 63 | | 40 | Seq | sense | 16990 | tgaggccacagtgactttg (19) | 136 |
| 64 | | 41 | Seq | sense | 17283 | cttctgagctcacaga (16) | 137 |
| 65 | | 41 | Seq | sense | 17354 | gacagagctgtgctgaga (18) | 138 |
| 66 | DH-58 | 40/41 | PCR | antisense | 17599 | tgagggaggtagaagccttg (20) | 139 |
| 67 | DH-59 | 40/41 | PCR | antisense | 17638 | cttcaggagagggcagacaag (21) | 140 |
| 68 | DH-60 | 42/43 | PCR | sense | 17580 | caaggcttctacctccctca (20) | 141 |
| 69 | DH-61 | 42 | Seq | sense | 17606 | tcaggaactgtccccttgt (19) | 142 |
| 70 | DH-62 | 42/43 | PCR | sense | 17618 | cttgtctgccctctcctgaag (21) | 143 |
| 71 | DH-63 | 43 | Seq | sense | 18046 | caaagtgtgagtgagttg (18) | 144 |
| 72 | | 42/43 | PCR | antisense | 18326 | tctaggctgagagagactttgttc (24) | 145 |
| 73 | | 42/43 | PCR | antisense | 18328 | ctttctaggctgagatgagacttg (23) | 146 |
| 74 | | 44/45 | PCR | sense | 18299 | gttggaacaagtctcatctca (21) | 147 |
| 76 | | 44 | Seq | sense | 18303 | gaacaagtctcatctca (17) | 148 |
| 75 | | 44 | Seq | sense | 18313 | catctcagcctagaag (16) | 149 |
| 77 | | 45 | Seq | sense | 18572 | cagtctctggactaag (16) | 150 |
| 78 | | 45 | Seq | sense | 18588 | gagcagtggcctcagatg (18) | 151 |
| 81 | DH-73 | 44/45 | PCR | antisense | 18840 | gtcccacccaagctgaggaatc (22) | 152 |
| 80 | | 44/45 | PCR | antisense | 18889 | gacagacaccgattgagtcaggtca (25) | 153 |
| 79 | | 44/45 | PCR | antisense | 18895 | gaacaagacagacaccgattg (21) | 154 |
| PB37 | | 46/47 | PCR | sense | 18571 | tccgcagtctctggactaag (20) | 155 |
| IH-37-1 | | 46 | Seq | sense | 18720 | tgagtatccaagtgtcctgc (20) | 156 |
| IH-38-B | | 47 | Seq | sense | 19206 | atatgtctgtgctgaccgtg (20) | 157 |
| IH-39 | | 46/47 | PCR | antisense | 19526 | tctgtctgacagcggaggca (20) | 158 |
| IH-38-A | * | 46 | Seq | sense | ? | gggattcctcagcctgggtg (20) | 159 |
| IH-40 | | 48/49 | PCR | sense | 19622 | actgagcatgtgaagaactg (20) | 160 |
| IH-41-A | | 48 | Seq | sense | 19661 | tatcaggacagccacctacc (20) | 161 |
| IH-41-B | | 49 | Seq | sense | 21027 | acactctagtacattctagc (20) | 162 |
| IH-42-A | | 48/49 | PCR | antisense | 20628 | aaccctctggcggaaacttc (20) | 163 |
| 82 | DH-74 | 49 | PCR | sense | 20042 | ctaaggaagaaatagacatg (20) | 164 |
| 83 | DH-75 | 49 | PCR | sense | 20047 | gaagaaatagacatggtgctgt (22) | 165 |
| 84 | DH-76 | 49 | Seq | sense | 20126 | gacactctagtacattc (17) | 166 |
| 85 | DH-77 | 49 | Seq | sense | 20130 | ctctagtacattctag (16) | 167 |
| 86 | DH-78 | 49 | Seq | sense | 20135 | gtacattctagcaaatg (17) | 168 |
| 87 | DH-79 | 49 | PCR | antisense | 20579 | catctcctcccttgctgctag (21) | 169 |
| PB42 | | 48/49 | PCR | antisense | 20720 | atggagtccaccctgaggtc (20) | 170 |
| IH-43-A | | 50/51 | PCR | sense | 20762 | cttagggctggacttagctc (20) | 171 |
| IH-43 | * | 50/51 | PCR | sense | 20849 | atcccttgtccctgtaggcc (20) | 172 |
| IH-44-A | | 50 | Seq | sense | 20883 | caggcctgggtctctcaagc (20) | 173 |
| IH-44-B | | 51 | Seq | sense | 21395 | ccttgaaccatgaactcttg (20) | 174 |
| IH-45-A | | 50/51 | PCR | antisense | 21892 | tctctcacctgtcactcagc (20) | 175 |
| IH-45 | * | 50/51 | PCR | antisense | 21895 | tctctcacctgtcactcagc (20) | 176 |
| IH-46 | | 52 | PCR | sense | 22098 | tggagaggcctttggcaagc (20) | 177 |
| IH-47 | | 52 | Seq | sense | 22158 | ttgtgggctctgatgctcgc (20) | 178 |
| IH-48 | | 52 | PCR | antisense | 22514 | tcaggtcagccattcagtgc (20) | 179 |

According to some embodiments:

SEQ ID NO:3 and SEQ ID NO:5 are used as PCR primers. The resulting PCR fragment is sequenced using SEQ ID:4 as the primer sequence.

SEQ ID NO:6 and SEQ ID NO:9 are used as PCR primers. The resulting PCR fragment is sequenced using SEQ ID:8 as the primer sequence.

SEQ ID NO:10 and SEQ ID NO:19 are used as PCR primers. The resulting PCR fragment is sequenced using SEQ ID:12 as the primer sequence.

SEQ ID NO:20 and SEQ ID NO:26 are used as PCR primers. The resulting PCR fragment is sequenced using SEQ ID:12 as the primer sequence.

SEQ ID NO:10 and SEQ ID NO:19 are used as PCR primers. The resulting PCR fragment is sequenced using SEQ ID:16 as the primer sequence.

SEQ ID NO:20 and SEQ ID NO:26 are used as PCR primers. The resulting PCR fragment is sequenced using SEQ ID:16 as the primer sequence.

SEQ ID NO:20 and SEQ ID NO:26 are used as PCR primers. The resulting PCR fragment is sequenced using SEQ ID:24 as the primer sequence.

SEQ ID NO:20 and SEQ ID NO:26 are used as PCR primers. The resulting PCR fragment is sequenced using SEQ ID:23 as the primer sequence.

SEQ ID NO:28 and SEQ ID NO:30 are used as PCR primers. The resulting PCR fragment is sequenced using SEQ ID:29 as the primer sequence.

SEQ ID NO:32 and SEQ ID NO:35 are used as PCR primers. The resulting PCR fragment is sequenced using SEQ ID:34 as the primer sequence.

SEQ ID NO:37 and SEQ ID NO:41 are used as PCR primers. The resulting PCR fragment is sequenced using SEQ ID:38 as the primer sequence.

SEQ ID NO:39 and SEQ ID NO:47 are used as PCR primers. The resulting PCR fragment is sequenced using SEQ ID:44 as the primer sequence.

SEQ ID NO:42 and SEQ ID NO:51 are used as PCR primers. The resulting PCR fragment is sequenced using SEQ ID:43 as the primer sequence.

SEQ ID NO:42 and SEQ ID NO:51 are used as PCR primers. The resulting PCR fragment is sequenced using SEQ ID:45 as the primer sequence.

SEQ ID NO:49 and SEQ ID NO:51 are used as PCR primers. The resulting PCR fragment is sequenced using SEQ ID:50 as the primer sequence.

SEQ ID NO:55 and SEQ ID NO:61 are used as PCR primers. The resulting PCR fragment is sequenced using SEQ ID:58 as the primer sequence.

SEQ ID NO:55 and SEQ ID NO:73 are used as PCR primers. The resulting PCR fragment is sequenced using SEQ ID:60 as the primer sequence.

SEQ ID NO:57 and SEQ ID NO:71 are used as PCR primers. The resulting PCR fragment is sequenced using SEQ ID:60 as the primer sequence.

SEQ ID NO:55 and SEQ ID NO:73 are used as PCR primers. The resulting PCR fragment is sequenced using SEQ ID:65 as the primer sequence.

SEQ ID NO:57 and SEQ ID NO:71 are used as PCR primers. The resulting PCR fragment is sequenced using SEQ ID:65 as the primer sequence.

SEQ ID NO:64 and SEQ ID NO:72 are used as PCR primers. The resulting PCR fragment is sequenced using SEQ ID:69 as the primer sequence.

SEQ ID NO:64 and SEQ ID NO:72 are used as PCR primers. The resulting PCR fragment is sequenced using SEQ ID:68 as the primer sequence.

SEQ ID NO:63 and SEQ ID NO:73 are used as PCR primers. The resulting PCR fragment is sequenced using SEQ ID:70 as the primer sequence.

SEQ ID NO:68 and SEQ ID NO:72 are used as PCR primers. The resulting PCR fragment is sequenced using SEQ ID:70 as the primer sequence.

SEQ ID NO:74 and SEQ ID NO:77 are used as PCR primers. The resulting PCR fragment is sequenced using SEQ ID:75 as the primer sequence.

SEQ ID NO:74 and SEQ ID NO:77 are used as PCR primers. The resulting PCR fragment is sequenced using SEQ ID:76 as the primer sequence.

SEQ ID NO:78 and SEQ ID NO:85 are used as PCR primers. The resulting PCR fragment is antisense sequenced using SEQ ID:81 as the primer sequence.

SEQ ID NO:79 and SEQ ID NO:84 are used as PCR primers. The resulting PCR fragment is antisense sequenced using SEQ ID:81 as the primer sequence.

SEQ ID NO:78 and SEQ ID NO:85 are used as PCR primers. The resulting PCR fragment is antisense sequenced using SEQ ID:83 as the primer sequence.

SEQ ID NO:79 and SEQ ID NO:84 are used as PCR primers. The resulting PCR fragment is antisense sequenced using SEQ ID:83 as the primer sequence.

SEQ ID NO:87 and SEQ ID NO:93 are used as PCR primers. The resulting PCR fragment is sequenced using SEQ ID:90 as the primer sequence.

SEQ ID NO:87 and SEQ ID NO:93 are used as PCR primers. The resulting PCR fragment is sequenced using SEQ ID:94 as the primer sequence.

SEQ ID NO:87 and SEQ ID NO:93 are used as PCR primers. The resulting PCR fragment is sequenced using SEQ ID:97 as the primer sequence.

SEQ ID NO:87 and SEQ ID NO:93 are used as PCR primers. The resulting PCR fragment is sequenced using SEQ ID:95 as the primer sequence.

SEQ ID NO:98 and SEQ ID NO:104 are used as PCR primers. The resulting PCR fragment is sequenced using SEQ ID:101 as the primer sequence.

SEQ ID NO:98 and SEQ ID NO:104 are used as PCR primers. The resulting PCR fragment is sequenced using SEQ ID:97 as the primer sequence.

SEQ ID NO:105 and SEQ ID NO:110 are used as PCR primers. The resulting PCR fragment is sequenced using SEQ ID:108 as the primer sequence.

SEQ ID NO:105 and SEQ ID NO:110 are used as PCR primers. The resulting PCR fragment is antisense sequenced using SEQ ID:109 as the primer sequence.

SEQ ID NO:112 and SEQ ID NO:116 are used as PCR primers. The resulting PCR fragment is sequenced using SEQ ID:113 as the primer sequence.

SEQ ID NO:112 and SEQ ID NO:116 are used as PCR primers. The resulting PCR fragment is sequenced using SEQ ID:114 as the primer sequence.

SEQ ID NO:117 and SEQ ID NO:122 are used as PCR primers. The resulting PCR fragment is sequenced using SEQ ID:119 as the primer sequence.

SEQ ID NO:117 and SEQ ID NO:121 are used as PCR primers. The resulting PCR fragment is sequenced using SEQ ID:120 as the primer sequence.

SEQ ID NO:117 and SEQ ID NO:122 are used as PCR primers. The resulting PCR fragment is sequenced using SEQ ID:119 as the primer sequence.

SEQ ID NO:117 and SEQ ID NO:121 are used as PCR primers. The resulting PCR fragment is sequenced using SEQ ID:120 as the primer sequence.

SEQ ID NO:123 and SEQ ID NO:132 are used as PCR primers. The resulting PCR fragment is sequenced using SEQ ID:125 as the primer sequence.

SEQ ID NO:123 and SEQ ID NO:132 are used as PCR primers. The resulting PCR fragment is sequenced using SEQ ID:129 as the primer sequence.

SEQ ID NO:134 and SEQ ID NO:140 are used as PCR primers. The resulting PCR fragment is sequenced using SEQ ID:137 as the primer sequence.

SEQ ID NO:135 and SEQ ID NO:139 are used as PCR primers. The resulting PCR fragment is sequenced using SEQ ID:137 as the primer sequence.

SEQ ID NO:134 and SEQ ID NO:140 are used as PCR primers. The resulting PCR fragment is sequenced using SEQ ID:136 as the primer sequence.

SEQ ID NO:134 and SEQ ID NO:140 are used as PCR primers. The resulting PCR fragment is sequenced using SEQ ID:138 as the primer sequence.

SEQ ID NO:135 and SEQ ID NO:139 are used as PCR primers. The resulting PCR fragment is sequenced using SEQ ID:136 as the primer sequence.

SEQ ID NO:135 and SEQ ID NO:139 are used as PCR primers. The resulting PCR fragment is sequenced using SEQ ID:138 as the primer sequence.

SEQ ID NO:141 and SEQ ID NO:145 are used as PCR primers. The resulting PCR fragment is sequenced using SEQ ID:143 as the primer sequence.

SEQ ID NO:143 and SEQ ID NO:146 are used as PCR primers. The resulting PCR fragment is sequenced using SEQ ID:143 as the primer sequence.

SEQ ID NO:141 and SEQ ID NO:145 are used as PCR primers. The resulting PCR fragment is sequenced using SEQ ID:144 as the primer sequence.

SEQ ID NO:143 and SEQ ID NO:146 are used as PCR primers. The resulting PCR fragment is sequenced using SEQ ID:144 as the primer sequence.

SEQ ID NO:147 and SEQ ID NO:153 are used as PCR primers. The resulting PCR fragment is sequenced using SEQ ID:148 as the primer sequence.

SEQ ID NO:147 and SEQ ID NO:154 are used as PCR primers. The resulting PCR fragment is sequenced using SEQ ID:148 as the primer sequence.

SEQ ID NO:147 and SEQ ID NO:152 are used as PCR primers. The resulting PCR fragment is sequenced using SEQ ID:148 as the primer sequence.

SEQ ID NO:147 and SEQ ID NO:153 are used as PCR primers. The resulting PCR fragment is sequenced using SEQ ID:151 as the primer sequence.

SEQ ID NO:147 and SEQ ID NO:154 are used as PCR primers. The resulting PCR fragment is sequenced using SEQ ID:151 as the primer sequence.

SEQ ID NO:147 and SEQ ID NO:152 are used as PCR primers. The resulting PCR fragment is sequenced using SEQ ID:151 as the primer sequence.

SEQ ID NO:155 and SEQ ID NO:158 are used as PCR primers. The resulting PCR fragment is sequenced using SEQ ID:156 as the primer sequence.

SEQ ID NO:155 and SEQ ID NO:158 are used as PCR primers. The resulting PCR fragment is sequenced using SEQ ID:157 as the primer sequence.

SEQ ID NO:160 and SEQ ID NO:163 are used as PCR primers. The resulting PCR fragment is sequenced using SEQ ID:161 as the primer sequence.

SEQ ID NO:160 and SEQ ID NO:170 are used as PCR primers. The resulting PCR fragment is sequenced using SEQ ID:162 as the primer sequence.

SEQ ID NO:160 and SEQ ID NO:163 are used as PCR primers. The resulting PCR fragment is sequenced using SEQ ID:4 as the primer sequence.

SEQ ID NO:160 and SEQ ID NO:170 are used as PCR primers. The resulting PCR fragment is sequenced using SEQ ID:4 as the primer sequence.

SEQ ID NO:171 and SEQ ID NO:176 are used as PCR primers. The resulting PCR fragment is sequenced using SEQ ID:174 as the primer sequence.

SEQ ID NO:171 and SEQ ID NO:176 are used as PCR primers. The resulting PCR fragment is sequenced as an antisense using SEQ ID:176 as the primer sequence.

SEQ ID NO:171 and SEQ ID NO:176 are used as PCR primers. The resulting PCR fragment is sequenced using SEQ ID:173 as the primer sequence.

SEQ ID NO:177 and SEQ ID NO:179 are used as PCR primers. The resulting PCR fragment is sequenced using SEQ ID:178 as the primer sequence.

Other examples of primers effective for amplification of sequences by PCR and sequencing of the PCR products presented in Table IA are within regions of the introns which have not been disclosed previously. These sequences and primers are included in the present invention. The steps whereby genomic DNA from an individual from sources such as white blood cells or any other cells in the body can be used in the procedure to detect variations in sequences are as follows. The DNA template is amplified using PCR. The PCR products can be loaded directly on an agarose gel and electrophoresed and analyzed or they can be diluted and subjected to a second round of PCR amplification. PCR products obtained from the first PCR reaction in which the regions of the gene symmetrically amplified were examined by electrophoresis in an agarose gel stained with ethidium bromide. The conditions of the experiment were adequate to generate an intense single band of DNA, an observation indicating that the target region was selectively amplified. If a second PCR amplification is carried out, the products are purified and sequenced. The second PCR in which the product of the first PCR is asymmetrically amplified generates a single-stranded DNA which can be directly used for sequencing. The results indicate the presence of two major bands of DNA, one double-stranded DNA and the second single-stranded DNA appropriate for sequencing. Analysis of the base sequences of PCR products from the second asymmetric PCR were analyzed by dideoxynucleotide sequencing using methods known in the art. The sequencing autoradiograms were of high enough quality to be able to detect single-base variations in which one allele of the gene has one base and the same position of the second allele from the same gene has a different base.

TABLE IA

| Region/ exon | 5'-Primer (sense) | 3'-Primer (antisense) | Product size |
| --- | --- | --- | --- |
| 1$^c$ | caactccggcagaactccg SEQ ID NO:262 | tatatctgtgcgcaaacttc SEQ ID NO:263 | 880 |
| 1 | agaagacgcagagcgctgct SEQ ID NO:264 | acagagtcttgattggcag SEQ ID NO:265 | 437 |
| 2A | ctcagcgtgcttcataggattc SEQ ID NO:266 | tctagtgtctcaggctcattcact SEQ ID NO:267 | 957 |
| 2B | ctgattagatcttgagctct SEQ ID NO:268 | ctggattaacatagcattgc SEQ ID NO:269 | 398 |
| 3 and 4 | gcaatgctatgttaatccag SEQ ID NO:270 | TCACCTTTGTCACCACGATC SEQ ID NO:271 | 478 |
| 5A and 5B | gctctctctcacagATTGTA SEQ ID NO:272 | gtaagtgcaagcagcaatt SEQ ID NO:273 | 548 |
| 6 | attgctgcttgcacttacctg SEQ ID NO:274 | agcaagaggttgtcagactct SEQ ID NO:275 | 1082 |
| 7 | gcagacagcagctactgttct SEQ ID NO:276 | atgaggataccaggtcaatc SEQ ID NO:277 | 484 |
| 8 | catcgtgtcgcagatgattc SEQ ID NO:278 | acagcagctgcgtcctagt SEQ ID NO:279 | 210 |
| 7 and 8 | gcagacagcagctactgttct SEQ ID NO:280 | acagcagctgcgtcctagt SEQ ID NO:281 | 623 |

TABLE IA-continued

| Exon No. | PCR Region | Primer Sequence | Comments |
|---|---|---|---|
| 1 | 1 | gcttcctcctcctgctccaag SEQ ID NO:282 | Antisense sequencing |
| 2A$^c$ | 2A | gagaccaggatatctga SEQ ID NO:283 | |
| 2B | 2B | gttcagtggagtcacagga SEQ ID NO:284 | |
| 3 | 3 and 4 | agttagaggagagcacaagga SEQ ID NO:285 | Antisense sequencing |
| 4 | 3 and 4 | tcgacgtcgtcgtcttaa SEQ ID NO:286 | |
| 5A | 5A and 5B | caagttactgatctgcagct SEQ ID NO:287 | |
| 5B | 5A and 5B | gacagatggctcttggagaa SEQ ID NO:.288 | |
| 6 | 6 | cagactctctggctctactaag SEQ ID NO:289 | Antisense sequencing |
| 7 | 7 | gcagctctgacttggcacat SEQ ID NO:290 | |
| | | atcatctgcgacacgatg SEQ ID NO:291 | Antisense sequencing |
| 8 | 8 | gtggtctatcattagaggct SEQ ID NO:292 | Antisense sequencing |
| 8 | 7 and 8 | catcgtgtcgcagatgattc SEQ ID NO:293 | |

According to some embodiments:

SEQ ID NO:262 and SEQ ID NO:263 are used as PCR primers. The resulting PCR fragment is antisense sequenced using SEQ ID:282 as the primer sequence.

SEQ ID NO:264 and SEQ ID NO:265 are used as PCR primers. The resulting PCR fragment is antisense sequenced using SEQ ID:282 as the primer sequence.

SEQ ID NO:266 and SEQ ID NO:267 are used as PCR primers. The resulting PCR fragment is sequenced using SEQ ID:283 as the primer sequence.

SEQ ID NO:268 and SEQ ID NO:269 are used as PCR primers. The resulting PCR fragment is sequenced using SEQ ID:284 as the primer sequence.

SEQ ID NO:270 and SEQ ID NO:271 are used as PCR primers. The resulting PCR fragment is antisense sequenced using SEQ ID:285 as the primer sequence.

SEQ ID NO:270 and SEQ ID NO:271 are used as PCR primers. The resulting PCR fragment is sequenced using SEQ ID:286 as the primer sequence.

SEQ ID NO:272 and SEQ ID NO:273 are used as PCR primers. The resulting PCR fragment is sequenced using SEQ ID:287 as the primer sequence.

SEQ ID NO:272 and SEQ ID NO:273 are used as PCR primers. The resulting PCR fragment is sequenced using SEQ ID:288 as the primer sequence.

SEQ ID NO:274 and SEQ ID NO:275 are used as PCR primers. The resulting PCR fragment is antisense sequenced using SEQ ID:289 as the primer sequence.

SEQ ID NO:276 and SEQ ID NO:277 are used as PCR primers. The resulting PCR fragment is sequenced using SEQ ID:290 as the primer sequence.

SEQ ID NO:276 and SEQ ID NO:277 are used as PCR primers. The resulting PCR fragment is antisense sequenced using SEQ ID:291 as the primer sequence.

SEQ ID NO:278 and SEQ ID NO:279 are used as PCR primers. The resulting PCR fragment is antisense sequenced using SEQ ID:292 as the primer sequence.

SEQ ID NO:280 and SEQ ID NO:281 are used as PCR primers. The resulting PCR fragment is sequenced using SEQ ID:293 as the primer sequence.

Figure 2:
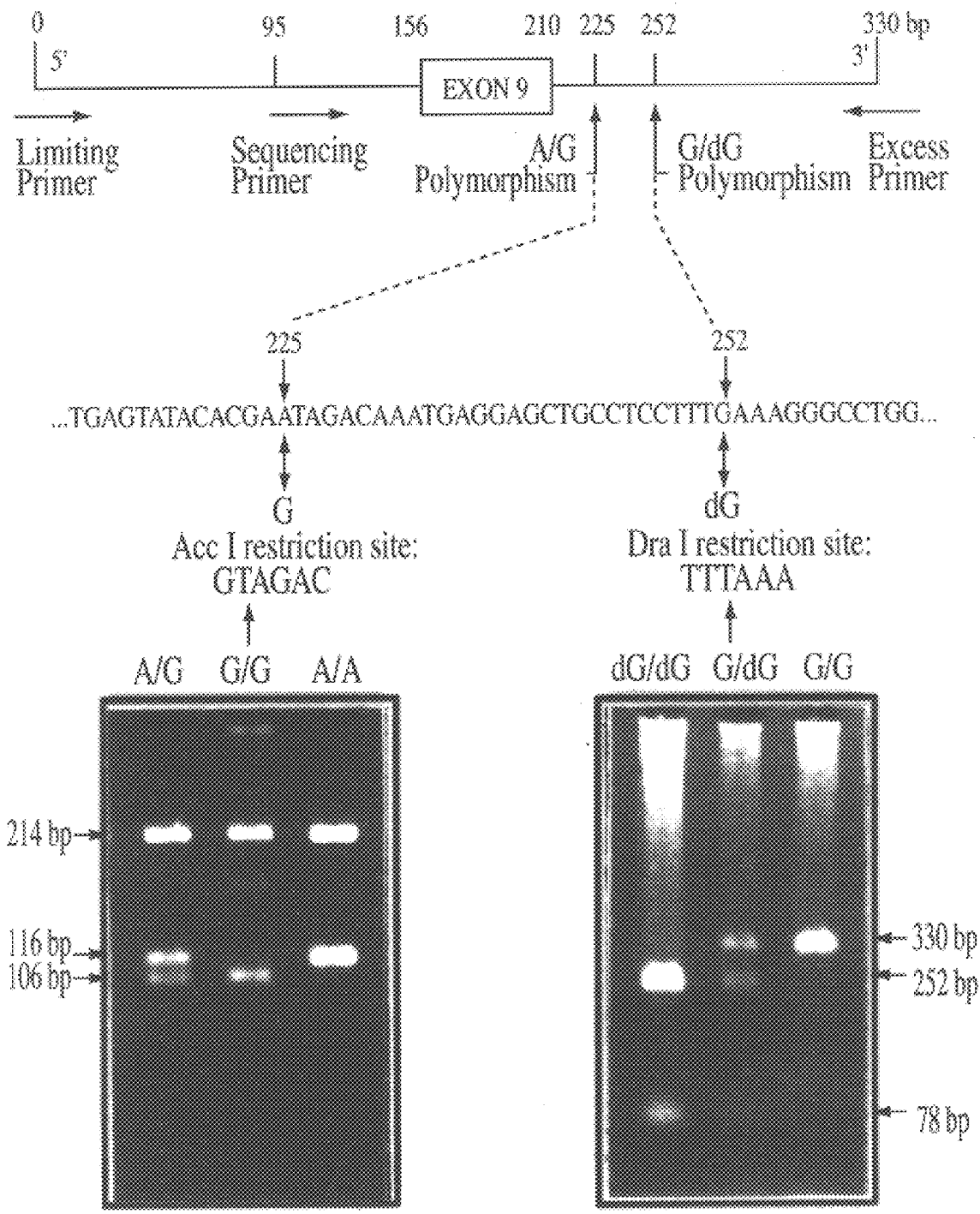
FIG. 2 shows a schematic for PCR amplification of COL2A1 exon 9 including the region of the gene comprising polymorphism 225 and 252 and agarose gels containing the amplification products.
Figure 3:
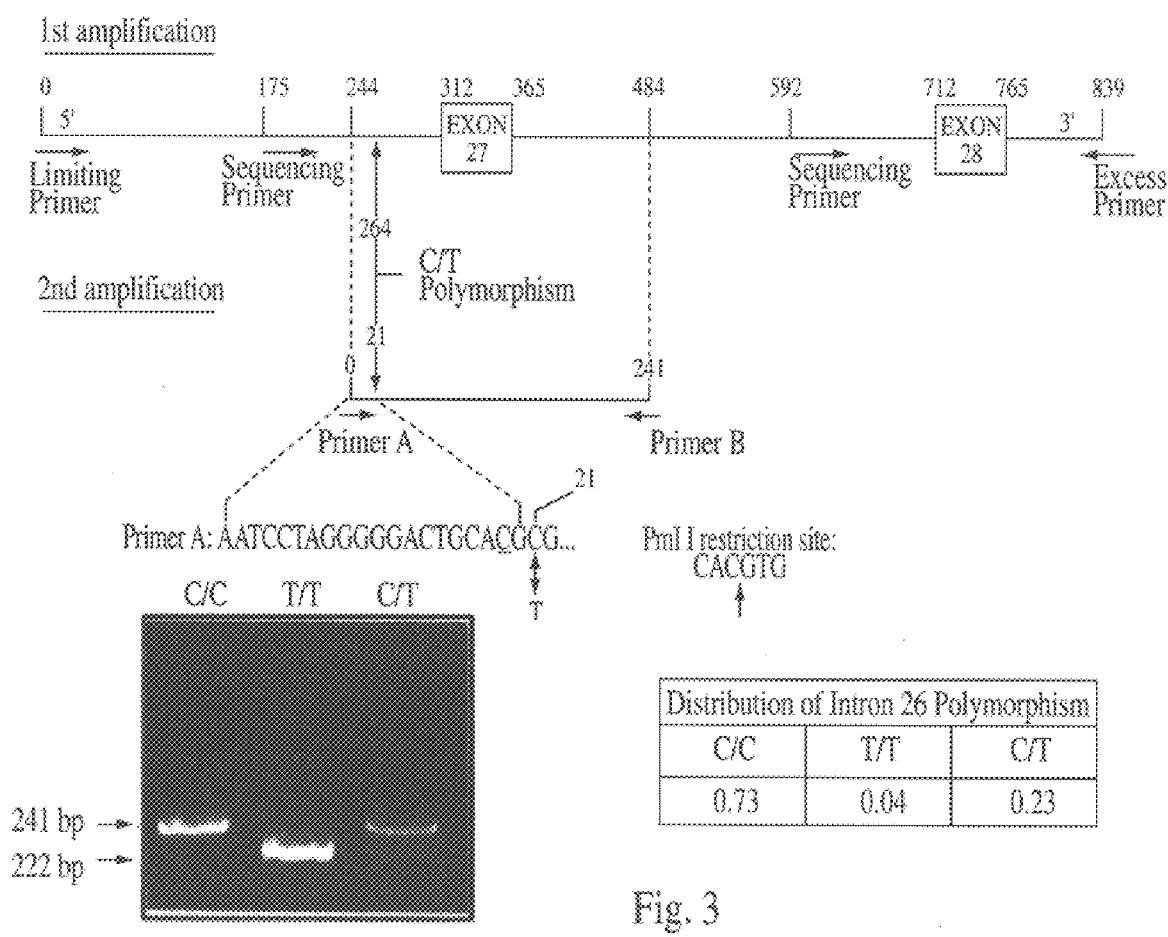
FIG. 3 shows a schematic for PCR amplification of COL2A1 exons 27 and 28 including the region of the gene comprising an intron 26 polymorphism and agarose gels containing the amplification products.

FIG. 2 demonstrates that the presence of single-base changes can in some instances be confirmed by digestion of the PCR product with restriction endonucleases. As shown in FIG. 2, the presence of variations at locations +15 (position 225 in FIG. 2) and +42 (position 252 in FIG. 2) of intron 9 can be distinguished by degeneration of one or two bands when the PCR products were digested either with restriction endonuclease Acc I or restriction endonuclease Dra I. As indicated in FIG. 3, the same approach can be used to confirm the presence of a base variation in intron 26 of the gene.

Table II summarizes the series of 21 sequence variations detected in analysis of alleles for COL2A1 from different individuals. None of the variations change coding sequences or other important sites in the genes such as consensus sites for RNA splicing. Therefore, they are probably all normal variations in the structure of the gene and not mutations that cause diseases.

TABLE II

TYPE II PROCOLLAGEN NEUTRAL SEQUENCE VARIANTS

| REGION | POSITION * | TYPE | ALLELES Major | ALLELES Minor | OBSERVED FREQUENCY | VERIFICATION |
|---|---|---|---|---|---|---|
| Exon 5B | 75 | base substitution | C | A | 0.25 | R.E. |
| Intron 9 | +15 | base substitution | G | A | 0.48 | R.E. |
| Intron 9 | +45 | base deletion | G | | 0.16 | R.E. |
| Exon 19 | 21 | base substitution | T | C | 0.02 | R.E |

TABLE II-continued

TYPE II PROCOLLAGEN NEUTRAL SEQUENCE VARIANTS

| REGION | POSITION * | TYPE | ALLELES Major | Minor | OBSERVED FREQUENCY | VERIFICATION |
|---|---|---|---|---|---|---|
| Exon 24 | 3 | base substitution | T | G | 0.01 | R.E. |
| Exon 26 | 3 | base substitution | T | C | 0.1 | PCR-1 R.E. |
| Intron 26 | −24 | base substitution | C | A | 0.1 | R.E. |
| Intron 26 | −47 | base substitution | C | T | 0.4 | PCR-1 R.E. |
| Exon 30 | 30 | base substitution | C | T | 0.03 | RSS |
| Intron 30 | +7 | base substitution | A | C | 0.1 | RSS |
| Intron 30 | +37 | base substitutian | G | T | 0.1 | RSS |
| Intron 31 | +7 | base substitution | G | A | 0.03 | RSS |
| Intron 31 | +56 | base substitution | C | T | 0.1 | R.E. |
| Intron 31 | +101 | base substitution | G | T/A | nd | RSS |
| Intron 31 | +128 | base deletion | G | | nd | RSS |
| Intron 31 | +183 | base substitution | C | T | 0.4 | RSS |
| Intron 31 | −55 | base substitution | T | G | 0.4 | RSS |
| Intron 31 | −56 | base deletion | G | | 0.4 | RSS |
| Exon 32 | 102 | base substitution | T | C | nd | R.E. |
| Intron 32 | −22 | base substitution | G | A | 0.04 | R.E. |
| Intron 32 | −32 | base substitution | T | C | 0.4 | R.E. | nd = not determined; RSS = reversed strand sequencing; R.E. = restriction enzyme analysis; PCR-1 R.E. = PCR-introduced restriction enzyme site analysis.
*Position for exon is designated without a ± sign. Position in intron is designated with a "−" sign if the sequence variant is located 5' to the next exon and with a "+" sign if the sequence variant is located 3' to the preceding exon.

Example 2

As a more rapid procedure for detecting sequence variations in the COL2A1 gene, a series of procedures were developed whereby the technique known as denaturing gradient gel electrophoresis (DGGE) could be used to analyze regions of the COL2A1 gene that were amplified by PCR. The technique makes it possible to determine which PCR amplified products from the two alleles have a single-base mutation and which do not. Therefore, the technique reduces the number of PCR products that must be analyzed by the more tedious procedure of nucleotide sequencing in order to determine whether or not a gene has a disease-causing mutation.

The technique of denaturing gradient gel electrophoresis was employed as described by Fischer and Lerman, *PNAS* 1983, 80, 1579; Myers et al., *Methods in Enzymology Vol. 155*, R. Wu, Ed., Academic Press, San Diego, 1987, pp 501–527; and Abrams et al., *Genomics* 1990, 7, 463–475. Procedures that are part of the present invention, however, involve the design and proof of efficacy of a series of primers that provide PCR products of sufficient quality for analysis by denaturing gradient gel electrophoresis. Also, the present invention defines conditions whereby the procedure is carried out so that sequence variations can be detected.

Table III presents the sequences and locations of the oligonucleotide primers used to produce PCR products adequate for analysis. Within each pair of primers, one primer contains a GC-rich sequence that serves as a "clamp" for denaturation and, thereby, greatly facilitates detection of a mutation in hybrid PCR products containing base sequences from both alleles.

TABLE III

PRIMERS AND CONDITIONS FOR PCR AMPLIFICATION OF THE COL2A1 AND ANALYSIS BY DGGE

| EXON | PRIMERS | product size (bp) | DGGE time (h) | SEQ ID NO |
|---|---|---|---|---|
| 5b | 5':GC-clamp + TCTTGGAGAAACACTGCTTCCCATTGATGC<br>3':AAAAGCCACATTTCTGGAGGGACAGCCTGA | 246 | 13 | 180<br>181 |
| 6 | 5':GC-clamp + CTAGTGCCTTTCAACCTCCTAACGTTG<br>3':AGGTTGTCAGACTCTCTGGCTCTACTAAG | 239 | 20 | 182<br>183 |
| 7 + 8 | 5':GC-clamp + GTAAACCCCTCATTTTCTGTTCCGATGC<br>3':CAGCTGCGTCCTAGTGGTCTATCATTAG | 349 | 20 | 184<br>185 |
| 9 | 5':GTCCATTGCTTAGGTGTCTTCCCACTA<br>3':GC-clamp + GGAGGCAGCTCCTCATTTGTCTACTC | 195 | 13 | 186<br>187 |
| 10 | 5':GC-clamp + CACTATGCTACGCGTCTCTGAGGAAGCT<br>3':CTCAGAAGTGACCTCATTGAACTGGATGC | 245 | 18 | 188<br>189 |

TABLE III-continued

PRIMERS AND CONDITIONS FOR PCR AMPLIFICATION
OF THE COL2A1 AND ANALYSIS BY DGGE

| EXON | PRIMERS | product size (bp) | DGGE time (h) | SEQ ID NO |
|---|---|---|---|---|
| 11 | 5':GC-clamp + CTCCTGCAGCCAGGGCAGCTTTCCACT<br>3':GGAAGAAATGCACGCACCCCAAAGTGC | 248 | 24 | 190<br>191 |
| 12 | 5':GC-clamp + CCAACTTGGGTTTCCCAGAAGTCTGA<br>3':TTGTCTCCCTCCTCCCCATCCCATTGTAC | 189 | 12 | 192<br>193 |
| 13 | 5':GC-clamp + ACCACTGAAGTTTGTGTCAGTGCGAGCT<br>3':TTTGCAGCCATCTGATAGTCTGAAGAGTC | 270 | 18 | 194<br>195 |
| 14 | 5':GC-clamp + CACCCTGAGCACCGTAAAGCCAACTCATG<br>3':CTATGCCTCACAGGTTTGTTTCGAGGGTCA | 248 | 16 | 196<br>197 |
| 15 | 5':TGCCTTCTGGCCACCCACTCGCACAGA<br>5':GC-clamp + CCACCCACTCGCACAGACACCAAAACTGCA<br>3': GTGGTTGCACCCAATACACCCTCGAGACTG | 352 | 20 | 198<br>199<br>200 |
| 16 | 5':GC-clamp + TTGCTTTGCCTTCTGAAGCCAGGCAAAGCT<br>3':AGCTTCTCGGCACCCAGAAGTTCCTGACT | 340 | 18 | 201<br>202 |
| 17 | 5':GC-clamp + TATTGCCCACCCACTAGAGGTCTGTGTC<br>3':CCCACAACTGTCAGAGCAAAGTACAGAGTC | 298 | 10 | 203<br>204 |
| 18 | 5':GC-clamp + GGTGGTTGGGGTTCATTCTTTGCTGCT<br>3':GGGCTCTCCTGGGGTAGCAAAGTCCAC | 177 | 14 | 205<br>206 |
| 19 | 5':GC-clamp + GGATCTGCTGTGAGTGTTGCCCGTGGACT<br>3':AGAGCATGGGAAAGAGGGGTGATG | 317 | 11 | 207<br>208 |
| 20 | 5':GC-clamp + TCCCTGGAGAGAATCTGGTGTGAGGACCT<br>3':CTCAGTCCCTGTTAAGTCTCCTCCAGGCAT | 425 | 17 | 209<br>210 |
| 21 | 5':GGCTACTTCCTTCATACTCTAGATCGA[b]<br>3':GC-clamp + CGGACCACAAGGACTCCACTTCCCTCTCGA[b] | 305 | 9 | 211<br>212 |
| 22 + 23 | 5':GC-clamp + CTGGCTGGGTTGGGCTGTTCTCACTCACTG<br>3':CTGAAGCCAAGGGCAACAGCAGCTCTGCTA | 366 | 14 | 213<br>214 |
| 24 | 5':GC-clamp + TAGCAGAGCTGCTGTTGCCCTTGGCTTCAG<br>3':ACCCTCCTAGCAGCCCTCAGAGGATAGACT | 260 | 10 | 215<br>216 |
| 25 | 3':CACTGTCCCTGGTTAAACTCTACTCAG<br>5':GC-clamp + GTCAATCCTAGATGCTGAGCATGTGTG | 375 | 19 | 217<br>218 |
| 26 | 5':GC-clamp + CATCAGGATGTGGCCCCAGGCTCAGTC<br>3': GGCCGTTCCCCTGTCCTCCCTGCAGAT | 264 | 11 | 219<br>220 |
| 27 | 5':GGAAACTCTGGGCCAGAAGTACCTTTG[c]<br>3': ATCAGCTCAGCCCACATTCACATCTCTCAG<br>3':GC-clamp + CCCAGCCCCCAGGGCACCTGGAGGCTG | 232 | 14 | 221<br>222<br>223 |
| 28 | 5':GC-clamp + AGTGCAGGGAGGCATGCATGCACTGTCTGA<br>3': TATGGCAAAGGACTGACACAGAGAGCCTG | 284 | 14 | 224<br>225 |
| 29 | 5':GC-clamp + TTCCCTGCACCCCTGGCTGTCACT<br>3':TGGAGGCTGGGACATGGGTCCAGA | 352 | 20 | 226<br>227 |

TABLE III-continued

PRIMERS AND CONDITIONS FOR PCR AMPLIFICATION OF THE COL2A1 AND ANALYSIS BY DGGE

| EXON | PRIMERS | product size (bp) | DGGE time (h) | SEQ ID NO |
|---|---|---|---|---|
| 30 | 5':CATGTCCCAGCCTCCACAGATGACACAAT<br>3':GC-clamp + GGCCCAAGGAGGCAGCCCGCATTGGC-CAACAG | 251 | 20 | 228<br>229 |
| 31 | 5':GC-clamp + CTTCTCCCCCACTGCTGTTGGTTGATCA<br>3':TACCACGAAGACCCCTACTGGATGCA | 226 | 8 | 230<br>231 |
| 32 | 5':GC-clamp + TTCAGGGAGAGGTGCTGTCCACTACAGACT<br>3':GCTCCTCAAAAAGGGCTAACAGAAACCTTCA | 325 | 19 | 232<br>233 |
| 33 | 5':GC-clamp + ACAGCAAATTCCTCTTGGGCAGGGACTG[d]<br>3':CAGTGGCAGACTGCCCAGACCCTCTCT | 308 | 20 | 234<br>235 |
| 34 | 5':GC-clamp + GACTTCTCTGTTAAAATGGGGCCAGAG<br>3':ACAGAACCCCTTTGGCAGGAGATAAGA | 316 | 9 | 236<br>237 |
| 35 | 5':AGGGTGCGGGTATGGGCTGCACAGTAA<br>3':GC-clamp + CTGCACTGACTCCCTGGCTCTCTGGTT | 319 | 12 | 238<br>239 |
| 36 | 5':GC-clamp + TCAGGGTGAGGGCTTTTGGGTTAACAGAG<br>3':TGGATGTGGAACTGGCCTGAGTGGAGGTA | 327 | 10.5 | 240<br>241 |
| 37 | 5':AGGACACACACGCAGATACTCACAGAGT<br>3':GC-clamp + CAGGAGCCCTTCCTTGAGGGAACAATTC | 299 | 10 | 242<br>243 |
| 38 | 5':CCTCTTCAGGCTGGGTTTTTAGTGCCA<br>3':GC-clamp + GGGGCCAGGCCTCTTTGTGAGGTGCAG | 283 | 24 | 244<br>245 |
| 39 | 5':CCCTTTCCATACCAGGCTCTGAGACCAC<br>3':GC-clamp + AGTGAAGGCCAGCCTGGAGCTCTCCAGA | 293 | 17 | 246<br>247 |
| 40 | 5':GC-clamp + TGAGGAAGGGTGAGATGAGTCCTCACT<br>3':CTACCCCATGCTCTGTGAGCTCAGAAG | 331 | 8 | 248<br>249 |
| 41 | 5':GC-clamp + CAGACAGAGCTGTGCTGAGAGGACGAAG<br>3':AGACAAGGGACAGTCCTGAGGGTGCTGA | 313 | 7 | 250<br>251 |
| 42 | 5':GCAGGGGTGCTTACCACTTGCACTCAT<br>3':GC-clamp + TCCTTGCTGACCCAGCACAGAGACTCAC | 274 | 10.5 | 252<br>253 |
| 43 | 5':GC-clamp + GGGCAGAAGAGGAGAGGCCTGGGCTTC<br>3': GTCCTTCTAGGCTGAGATGAGACTTGT | 309 | 8 | 254<br>255 |
| 44 | 5':GC-clamp + GGAACATTCTTCTCTGAGCCTGAGAC<br>3':CAGGGGAAGGCGGCTTTTACTGAATTC | 227 | 9 | 256<br>257 |
| 45 + 46 | 5':GC-clamp + CTGGACTAAGGAGCAGTGGCCTCAGAT<br>3': CAGCCCTGAGGAAATCCTAGAAACTGC | 595 | 12.5 | 258<br>259 |
| 47 | 5':AATATAGATAGATATGTCTGTGCTGAC<br>3':GC-clamp + GGCCCCCTCCATCTTCCAACTCCATG | 185 | 10 | 260<br>261 |

[a]GC-clamp:CCGCCCGCCCCGCCCGCCGCCCGCCCCGCCCGCCGCCCGC
[b]40 pmols of primer. Twenty pmols of all other primers.
[c]Primers I and II were used for first PCR amplification and primers I and III were used for the second.
[d]Annealing temperature was 60° C. instead of 54° C.

The present invention also provides the running times for denaturing gradient gel electrophoresis that are critical for successful analysis of each of the PCR products.

Table IV illustrates the sequence variations detected by the technique. As indicated, five single-base differences were observed within introns of the COL2A1 gene and five within coding exons of the gene. The presence of the sequence variations was confirmed by dideoxynucleotide sequencing of the PCR products as described in Example 1.

TABLE IV

SEQUENCE VARIANTS DETECTED IN COL2A1 GENE

| INTRON | POSITION | VARIATION |
|---|---|---|
| 19 | −11 | C/T |
| 24 | −24 | C/T |
| 26 | −24 | C/A |
| 32 | +69 | C/T[a] |
| 32 | −22 | G/A |

AMINO ACID

| exon | codon | Variation |
|---|---|---|
| 5B | Gly | C/A[a] |
| 26 | Gly 412 | C/T |
| 31 | Arg → Cys 519 | C/T |
| 32 | Gly 565 | C/T |
| 34 | Asn 600 | C/T |

[a]New sequence variations detected here.

Example 3

Methods of the present invention were used to analyze the COL2A1 gene in a proband with arthro-ophthalmopathy or the Wagner-Stickler syndrome.

The proband was a male who at the age of three had severe myopia and incipient posterior cataracts. He had mild mid-facial hypoplasia. His knees, elbows and ankle joints were slightly hyperextensible. By the age of eight years, the vision in the left eye had deteriorated because of a cataract. The cataract was removed by suction. Two weeks later he had retinal ablation of the left eye. The other retina was then cryocoagulated. The proband's mother and proband's maternal uncle had similar problems. The proband's maternal grandfather also appeared to have manifestations of the disease since he had retinal ablation in one eye after a fall at the age of 18 and ophthalmologic examination at the age of 23 demonstrated he had a cataract in one eye and very limited vision in both eyes.

Methods of the present invention were used to amplify 15 of the 54 exons of the COL2A1 gene and then to analyze the PCR products by denaturing gradient gel electrophoresis. The results suggested the presence of a mutation in a PCR product containing base sequences from exon 10.

Dideoxynucleotide sequencing of the PCR products from exon 10 demonstrated the proband had both a G and an A in the second base for the codon at position $\alpha 1$-67 of the $\alpha 1(II)$ chain of type II collagen. The G makes the codon -GTT- for glycine, the normal amino acid present at this position. The A makes the codon -GAT-, a codon for aspartate, an amino acid that is never found in this, the third position in the repeating -Gly-X-Y- sequence of the $\alpha$ chain domain of a collagen. Extensive analysis of genes of fibrillar collagens in a large number of people have demonstrated that the third position in the repeating -Gly-X-Y- sequence of collagen is always glycine.

Examination of exon 10 from the proband's mother and maternal uncle demonstrated that they also had the same mutation. Unaffected members of the family did not have the mutation. Also, examination of exon 10 from 46 unrelated individuals demonstrated that they did not have the mutation at amino acid position $\alpha 1$-67. The results, therefore, establish that the mutation at position $\alpha 1$-67 was the cause of arthro-ophthalmopathy in the proband. The discovery of the mutation makes it possible to offer a prenatal diagnostic test to the family.

What is claimed is:

1. A method of determining a genetic predisposition for a disease in a human individual caused by a mutation in a region of COL2A1, said method comprising:

obtaining a cell from said individual;

isolating a nucleic acid from said cell, wherein said nucleic acid comprises said region;

amplifying said region using a first primer, wherein said first primer has a nucleotide sequence selected from the group consisting of SEQ ID NOs 28–44, 47–66, 68–80, 83, 85, 86, 112–143, 145, and 158; and detecting the presence or absence of said mutation in said region, whereby the presence of said mutation in said region indicates a genetic predisposition for said disease.

2. The method of claim 1, wherein said disease is selected from the group consisting of osteoarthritis, chondrodysplasia, dwarfism, malformation of joints, myopia, retinal detachment, blindness, cataracts, and cleft palate.

3. The method of claim 2, wherein said disease is osteoarthritis.

4. The method of claim 1, wherein said first primer has a nucleotide sequence selected from the group consisting of

141

SEQ ID NOs: 28–44, 47–59, 61–66, 69, 70, 72–80, 83, 86, 112–143, 145, and 158.

5. The method of claim 1, wherein said first primer has a nucleotide sequence selected from the group consisting of SEQ ID NOs: 28–44, 48–58, 61–66, 70, 72–80, 83, 86, 112–118, 120–124, 126–138, 140, and 143.

6. The method of claim 1, wherein said first primer has a nucleotide sequence selected from the group consisting of SEQ ID NOs: 28, 30–37, 39–42, 47–49, 51–57, 61–64, 72–74, 77–79, 86, 112, 115–118, 121–124, 126–128, 130–135, 139–141, 143, 145, and 158.

7. The method of claim 1, wherein said first primer has a nucleotide sequence selected from the group consisting of SEQ ID NOs: 28, 30–37, 39–42, 48, 49, 51–57, 61–64, 72–74, 77–79, 112, 115–118, 121–124, 126–128, 130–135, 140, and 143.

8. The method of claim 1, wherein detecting the presence or absence of said mutation in said region comprises determining the nucleotide sequence of said region using a sequencing primer, wherein said sequencing primer has a nucleotide sequence selected from the group consisting of SEQ ID NOs: 4, 7, 8, 11–17, 21–25, 27, 29, 38, 43–46, 50, 58–60, 64–70, 75, 76, 80–83, 88, 91, 92, 94–97, 99–101, 107–109, 113, 114, 119, 120, 125, 129, 136–138, 142, 144, 148–151, 156, 157, 159, 161, 162, 166–168, 173, 174, and 178.

9. The method of claim 8, wherein said sequencing primer has a nucleotide sequence selected from the group consisting of SEQ ID NOs: 29, 38, 43–44, 50, 58–60, 64–66, 68–70, 75, 76, 80, 83, 113, 114, 119, 120, 125, 129, 136–138, and 142.

10. A method of determining a genetic predisposition for a disease in a human individual caused by a mutation in a region of COL2A1, said method comprising:

obtaining a cell from said individual;

isolating a nucleic acid from said cell, wherein said nucleic acid comprises said region;

amplifying said region using a first primer and a second primer, wherein said first primer and said second primer are selected such that when said first primer has a nucleotide sequence listed in Column 1 of the following table, said second primer has the nucleotide sequence listed on the same row in Column 2 of the table:

| Column 1 | Column 2 |
|---|---|
| SEQ ID NO: 2 | SEQ ID NO: 5 |
| SEQ ID NO: 3 | SEQ ID NO: 5 |
| SEQ ID NO: 6 | SEQ ID NO: 9 |
| SEQ ID NO: 10 | SEQ ID NO: 18 |
| SEQ ID NO: 10 | SEQ ID NO: 19 |
| SEQ ID NO: 20 | SEQ ID NO: 26 |
| SEQ ID NO: 28 | SEQ ID NO: 30 |
| SEQ ID NO: 28 | SEQ ID NO: 31 |
| SEQ ID NO: 32 | SEQ ID NO: 35 |
| SEQ ID NO: 33 | SEQ ID NO: 35 |
| SEQ ID NO: 34 | SEQ ID NO: 35 |
| SEQ ID NO: 32 | SEQ ID NO: 36 |
| SEQ ID NO: 33 | SEQ ID NO: 36 |
| SEQ ID NO: 34 | SEQ ID NO: 36 |
| SEQ ID NO: 37 | SEQ ID NO: 40 |
| SEQ ID NO: 39 | SEQ ID NO: 40 |
| SEQ ID NO: 37 | SEQ ID NO: 41 |
| SEQ ID NO: 39 | SEQ ID NO: 41 |
| SEQ ID NO: 39 | SEQ ID NO: 47 |
| SEQ ID NO: 39 | SEQ ID NO: 48 |
| SEQ ID NO: 42 | SEQ ID NO: 47 |
| SEQ ID NO: 42 | SEQ ID NO: 48 |

142

-continued

| Column 1 | Column 2 |
|---|---|
| SEQ ID NO: 49 | SEQ ID NO: 51 |
| SEQ ID NO: 49 | SEQ ID NO: 52 |
| SEQ ID NO: 49 | SEQ ID NO: 53 |
| SEQ ID NO: 49 | SEQ ID NO: 54 |
| SEQ ID NO: 55 | SEQ ID NO: 61 |
| SEQ ID NO: 55 | SEQ ID NO: 62 |
| SEQ ID NO: 55 | SEQ ID NO: 71 |
| SEQ ID NO: 55 | SEQ ID NO: 72 |
| SEQ ID NO: 55 | SEQ ID NO: 73 |
| SEQ ID NO: 56 | SEQ ID NO: 61 |
| SEQ ID NO: 56 | SEQ ID NO: 62 |
| SEQ ID NO: 56 | SEQ ID NO: 71 |
| SEQ ID NO: 56 | SEQ ID NO: 72 |
| SEQ ID NO: 56 | SEQ ID NO: 73 |
| SEQ ID NO: 57 | SEQ ID NO: 61 |
| SEQ ID NO: 57 | SEQ ID NO: 62 |
| SEQ ID NO: 57 | SEQ ID NO: 71 |
| SEQ ID NO: 57 | SEQ ID NO: 72 |
| SEQ ID NO: 57 | SEQ ID NO: 73 |
| SEQ ID NO: 63 | SEQ ID NO: 61 |
| SEQ ID NO: 63 | SEQ ID NO: 62 |
| SEQ ID NO: 63 | SEQ ID NO: 71 |
| SEQ ID NO: 63 | SEQ ID NO: 72 |
| SEQ ID NO: 63 | SEQ ID NO: 73 |
| SEQ ID NO: 64 | SEQ ID NO: 61 |
| SEQ ID NO: 64 | SEQ ID NO: 62 |
| SEQ ID NO: 64 | SEQ ID NO: 71 |
| SEQ ID NO: 64 | SEQ ID NO: 72 |
| SEQ ID NO: 64 | SEQ ID NO: 73 |
| SEQ ID NO: 74 | SEQ ID NO: 77 |
| SEQ ID NO: 78 | SEQ ID NO: 84 |
| SEQ ID NO: 78 | SEQ ID NO: 85 |
| SEQ ID NO: 79 | SEQ ID NO: 84 |
| SEQ ID NO: 79 | SEQ ID NO: 85 |
| SEQ ID NO: 86 | SEQ ID NO: 84 |
| SEQ ID NO: 86 | SEQ ID NO: 85 |
| SEQ ID NO: 87 | SEQ ID NO: 93 |
| SEQ ID NO: 89 | SEQ ID NO: 93 |
| SEQ ID NO: 90 | SEQ ID NO: 93 |
| SEQ ID NO: 87 | SEQ ID NO: 102 |
| SEQ ID NO: 89 | SEQ ID NO: 102 |
| SEQ ID NO: 90 | SEQ ID NO: 102 |
| SEQ ID NO: 87 | SEQ ID NO: 103 |
| SEQ ID NO: 89 | SEQ ID NO: 103 |
| SEQ ID NO: 90 | SEQ ID NO: 103 |
| SEQ ID NO: 97 | SEQ ID NO: 102 |
| SEQ ID NO: 97 | SEQ ID NO: 103 |
| SEQ ID NO: 97 | SEQ ID NO: 104 |
| SEQ ID NO: 98 | SEQ ID NO: 102 |
| SEQ ID NO: 98 | SEQ ID NO: 103 |
| SEQ ID NO: 98 | SEQ ID NO: 104 |
| SEQ ID NO: 105 | SEQ ID NO: 110 |
| SEQ ID NO: 106 | SEQ ID NO: 110 |
| SEQ ID NO: 111 | SEQ ID NO: 115 |
| SEQ ID NO: 111 | SEQ ID NO: 116 |
| SEQ ID NO: 112 | SEQ ID NO: 115 |
| SEQ ID NO: 112 | SEQ ID NO: 116 |
| SEQ ID NO: 117 | SEQ ID NO: 121 |
| SEQ ID NO: 117 | SEQ ID NO: 122 |
| SEQ ID NO: 118 | SEQ ID NO: 121 |
| SEQ ID NO: 118 | SEQ ID NO: 122 |
| SEQ ID NO: 123 | SEQ ID NO: 131 |
| SEQ ID NO: 123 | SEQ ID NO: 132 |
| SEQ ID NO: 123 | SEQ ID NO: 133 |
| SEQ ID NO: 124 | SEQ ID NO: 131 |
| SEQ ID NO: 124 | SEQ ID NO: 132 |
| SEQ ID NO: 124 | SEQ ID NO: 133 |
| SEQ ID NO: 126 | SEQ ID NO: 131 |
| SEQ ID NO: 126 | SEQ ID NO: 132 |
| SEQ ID NO: 126 | SEQ ID NO: 133 |
| SEQ ID NO: 127 | SEQ ID NO: 131 |
| SEQ ID NO: 127 | SEQ ID NO: 132 |
| SEQ ID NO: 127 | SEQ ID NO: 133 |
| SEQ ID NO: 128 | SEQ ID NO: 131 |
| SEQ ID NO: 128 | SEQ ID NO: 132 |
| SEQ ID NO: 128 | SEQ ID NO: 133 |
| SEQ ID NO: 130 | SEQ ID NO: 131 |
| SEQ ID NO: 130 | SEQ ID NO: 132 |

| Column 1 | Column 2 |
| --- | --- |
| SEQ ID NO: 130 | SEQ ID NO: 133 |
| SEQ ID NO: 134 | SEQ ID NO: 139 |
| SEQ ID NO: 134 | SEQ ID NO: 140 |
| SEQ ID NO: 135 | SEQ ID NO: 139 |
| SEQ ID NO: 135 | SEQ ID NO: 140 |
| SEQ ID NO: 141 | SEQ ID NO: 145 |
| SEQ ID NO: 141 | SEQ ID NO: 146 |
| SEQ ID NO: 143 | SEQ ID NO: 145 |
| SEQ ID NO: 143 | SEQ ID NO: 146 |
| SEQ ID NO: 147 | SEQ ID NO: 152 |
| SEQ ID NO: 147 | SEQ ID NO: 153 |
| SEQ ID NO: 147 | SEQ ID NO: 154 |
| SEQ ID NO: 155 | SEQ ID NO: 158 |
| SEQ ID NO: 160 | SEQ ID NO: 163 |
| SEQ ID NO: 160 | SEQ ID NO: 169 |
| SEQ ID NO: 160 | SEQ ID NO: 170 |
| SEQ ID NO: 164 | SEQ ID NO: 163 |
| SEQ ID NO: 164 | SEQ ID NO: 169 |
| SEQ ID NO: 164 | SEQ ID NO: 170 |
| SEQ ID NO: 165 | SEQ ID NO: 163 |
| SEQ ID NO: 165 | SEQ ID NO: 169 |
| SEQ ID NO: 165 | SEQ ID NO: 170 |
| SEQ ID NO: 171 | SEQ ID NO: 175 |
| SEQ ID NO: 171 | SEQ ID NO: 176 |
| SEQ ID NO: 172 | SEQ ID NO: 175 |
| SEQ ID NO: 172 | SEQ ID NO: 176 |
| SEQ ID NO: 177 | SEQ ID NO: 179. |

11. The method of claim 10, wherein said first primer and said second primer are selected such that when said first primer has a nucleotide sequence listed in Column 1 of the following table, said second primer has the nucleotide sequence listed on the same row in Column 2 of the table:

| Column 1 | Column 2 |
| --- | --- |
| SEQ ID NO: 28 | SEQ ID NO: 30 |
| SEQ ID NO: 28 | SEQ ID NO: 31 |
| SEQ ID NO: 32 | SEQ ID NO: 35 |
| SEQ ID NO: 33 | SEQ ID NO: 35 |
| SEQ ID NO: 34 | SEQ ID NO: 35 |
| SEQ ID NO: 32 | SEQ ID NO: 36 |
| SEQ ID NO: 33 | SEQ ID NO: 36 |
| SEQ ID NO: 34 | SEQ ID NO: 36 |
| SEQ ID NO: 37 | SEQ ID NO: 40 |
| SEQ ID NO: 39 | SEQ ID NO: 40 |
| SEQ ID NO: 37 | SEQ ID NO: 41 |
| SEQ ID NO: 39 | SEQ ID NO: 41 |
| SEQ ID NO: 39 | SEQ ID NO: 47 |
| SEQ ID NO: 39 | SEQ ID NO: 48 |
| SEQ ID NO: 42 | SEQ ID NO: 47 |
| SEQ ID NO: 42 | SEQ ID NO: 48 |
| SEQ ID NO: 49 | SEQ ID NO: 51 |
| SEQ ID NO: 49 | SEQ ID NO: 52 |
| SEQ ID NO: 49 | SEQ ID NO: 53 |
| SEQ ID NO: 49 | SEQ ID NO: 54 |
| SEQ ID NO: 55 | SEQ ID NO: 61 |
| SEQ ID NO: 55 | SEQ ID NO: 62 |
| SEQ ID NO: 55 | SEQ ID NO: 71 |
| SEQ ID NO: 55 | SEQ ID NO: 72 |
| SEQ ID NO: 55 | SEQ ID NO: 73 |
| SEQ ID NO: 56 | SEQ ID NO: 61 |
| SEQ ID NO: 56 | SEQ ID NO: 62 |
| SEQ ID NO: 56 | SEQ ID NO: 71 |
| SEQ ID NO: 56 | SEQ ID NO: 72 |
| SEQ ID NO: 56 | SEQ ID NO: 73 |
| SEQ ID NO: 57 | SEQ ID NO: 61 |
| SEQ ID NO: 57 | SEQ ID NO: 62 |
| SEQ ID NO: 57 | SEQ ID NO: 71 |
| SEQ ID NO: 57 | SEQ ID NO: 72 |
| SEQ ID NO: 57 | SEQ ID NO: 73 |
| SEQ ID NO: 63 | SEQ ID NO: 61 |
| SEQ ID NO: 63 | SEQ ID NO: 62 |
| SEQ ID NO: 63 | SEQ ID NO: 71 |
| SEQ ID NO: 63 | SEQ ID NO: 72 |
| SEQ ID NO: 63 | SEQ ID NO: 73 |
| SEQ ID NO: 64 | SEQ ID NO: 61 |
| SEQ ID NO: 64 | SEQ ID NO: 62 |
| SEQ ID NO: 64 | SEQ ID NO: 71 |
| SEQ ID NO: 64 | SEQ ID NO: 72 |
| SEQ ID NO: 64 | SEQ ID NO: 73 |
| SEQ ID NO: 74 | SEQ ID NO: 77 |
| SEQ ID NO: 78 | SEQ ID NO: 84 |
| SEQ ID NO: 78 | SEQ ID NO: 85 |
| SEQ ID NO: 79 | SEQ ID NO: 84 |
| SEQ ID NO: 79 | SEQ ID NO: 85 |
| SEQ ID NO: 86 | SEQ ID NO: 84 |
| SEQ ID NO: 86 | SEQ ID NO: 85 |
| SEQ ID NO: 111 | SEQ ID NO: 115 |
| SEQ ID NO: 111 | SEQ ID NO: 116 |
| SEQ ID NO: 112 | SEQ ID NO. 115 |
| SEQ ID NO: 112 | SEQ ID NO: 116 |
| SEQ ID NO: 117 | SEQ ID NO: 121 |
| SEQ ID NO: 117 | SEQ ID NO: 122 |
| SEQ ID NO: 118 | SEQ ID NO: 121 |
| SEQ ID NO: 118 | SEQ ID NO: 122 |
| SEQ ID NO: 123 | SEQ ID NO: 131 |
| SEQ ID NO: 123 | SEQ ID NO: 132 |
| SEQ ID NO: 123 | SEQ ID NO: 133 |
| SEQ ID NO: 124 | SEQ ID NO: 131 |
| SEQ ID NO: 124 | SEQ ID NO: 132 |
| SEQ ID NO: 124 | SEQ ID NO: 133 |
| SEQ ID NO: 126 | SEQ ID NO: 131 |
| SEQ ID NO: 126 | SEQ ID NO: 132 |
| SEQ ID NO: 126 | SEQ ID NO: 133 |
| SEQ ID NO: 127 | SEQ ID NO: 131 |
| SEQ ID NO: 127 | SEQ ID NO: 132 |
| SEQ ID NO: 127 | SEQ ID NO: 133 |
| SEQ ID NO: 128 | SEQ ID NO: 131 |
| SEQ ID NO: 128 | SEQ ID NO: 132 |
| SEQ ID NO: 128 | SEQ ID NO: 133 |
| SEQ ID NO: 130 | SEQ ID NO: 131 |
| SEQ ID NO: 130 | SEQ ID NO: 132 |
| SEQ ID NO: 130 | SEQ ID NO: 133 |
| SEQ ID NO: 134 | SEQ ID NO: 139 |
| SEQ ID NO: 134 | SEQ ID NO: 140 |
| SEQ ID NO: 135 | SEQ ID NO: 139 |
| SEQ ID NO: 135 | SEQ ID NO: 140 |
| SEQ ID NO: 141 | SEQ ID NO: 145 |
| SEQ ID NO: 141 | SEQ ID NO: 146 |
| SEQ ID NO: 143 | SEQ ID NO: 145 |
| SEQ ID NO: 143 | SEQ ID NO: 146 |
| SEQ ID NO: 155 | SEQ ID NO: 158. |

12. A primer, wherein said primer is complementary to an intronic sequence of COL2A1 and has a nucleotide sequence selected from the group consisting of SEQ ID NOs: 28–44, 47–66, 68–80, 83, 85, 86, 112–143, 145, and 158.

13. The primer of claim 12, wherein said primer has a nucleotide sequence selected from the group consisting of SEQ ID NOs: 28–44, 47–59, 61–66, 69, 70, 72–80, 83, 86, 112–143, 145, and 158.

14. The primer of claim 12, wherein said primer has a nucleotide sequence selected from the group consisting of SEQ ID NOs: 28–44, 48–58, 61–66, 70, 72–80, 83, 86, 112–118, 120–124, 126–138, 140, and 143.

15. The primer of claim 12, wherein said primer has a nucleotide sequence selected from the group consisting of SEQ ID NOs: 28, 30–37, 39–42, 47–49, 51–57, 61–64, 72–74, 77–79, 86, 112, 115–118, 121–124, 126–128, 130–135, 139–141, 143, 145, and 158.

16. The primer of claim 12, wherein said primer has a nucleotide sequence selected from the group consisting of SEQ ID NOs: 28, 30–37, 39–42, 48, 49, 51–57, 61–64, 72–74, 77–79, 112, 115–118, 121–124, 126–128, 130–135, 140, and 143.

17. The method of claim 1, further comprising amplifying said region using a second primer, wherein said second primer has a nucleotide sequence selected from the group consisting of SEQ ID NOs: 1–179.

18. The primer of claim 12, wherein said primer has a nucleotide sequence selected from the group consisting of SEQ ID NOs: 28, 30–37, 39–42, 48, 49, and 51–57.

19. The primer of claim 12, wherein said primer has a nucleotide sequence selected from the group consisting of SEQ ID NOs: 61–64, 72–74, 77–79, 112, 115–118, and 121–124.

20. The primer of claim 12, wherein said primer has a nucleotide sequence selected from the group consisting of SEQ ID NOs: 126–128, 130–135, 140, and 143.

* * * * *